United States Patent
Mizusaki et al.

(10) Patent No.: US 12,017,208 B2
(45) Date of Patent: Jun. 25, 2024

(54) CROSS-COUPLING REACTION CATALYST

(71) Applicants: N.E. CHEMCAT CORPORATION, Tokyo (JP); NATIONAL INSTITUTE OF ADVANCED INDUSTRIAL SCIENCE AND TECHNOLOGY, Tokyo (JP)

(72) Inventors: Tomoteru Mizusaki, Tokyo (JP); Yukio Takagi, Tokyo (JP); Junchul Choi, Tsukuba (JP); Norihisa Fukaya, Tsukuba (JP); Kazuhiro Matsumoto, Tsukuba (JP)

(73) Assignees: N.E. CHEMCAT CORPORATION, Tokyo (JP); NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 0 days.

(21) Appl. No.: 17/269,093

(22) PCT Filed: Aug. 28, 2019

(86) PCT No.: PCT/JP2019/033648
§ 371 (c)(1),
(2) Date: Feb. 17, 2021

(87) PCT Pub. No.: WO2020/045476
PCT Pub. Date: Mar. 5, 2020

(65) Prior Publication Data
US 2021/0308660 A1 Oct. 7, 2021

(30) Foreign Application Priority Data
Aug. 31, 2018 (JP) ................. 2018-163367

(51) Int. Cl.
*B01J 31/22* (2006.01)
*C07C 209/10* (2006.01)

(52) U.S. Cl.
CPC ............ *B01J 31/22* (2013.01); *C07C 209/10* (2013.01); *B01J 2531/824* (2013.01)

(58) Field of Classification Search
None
See application file for complete search history.

(56) References Cited

FOREIGN PATENT DOCUMENTS

| CA | 2551412 | * | 2/2007 |
| WO | 2007/017047 A1 | | 2/2007 |

(Continued)

OTHER PUBLICATIONS

Dalton Transactions, 2014, 43, 13704 (Year: 2014).*

(Continued)

*Primary Examiner* — Yun Qian
(74) *Attorney, Agent, or Firm* — WHDA, LLP

(57) ABSTRACT

It is an object of the present invention to provide a catalyst for a cross-coupling reaction in which an organometallic complex is sufficiently immobilized on a carrier and an object product can be easily obtained in a high yield and in a relatively short reaction time with a relatively small amount of use. The catalyst for a cross-coupling reaction of the present invention has a carrier part composed of a synthetic resin and an organometallic complex part immobilized on the carrier part by chemical bonding, and has a structure represented by formula (P1), wherein in (P1) $R^1$, $R^2$ may be the same or different, and is a substituent such as a hydrogen atom. $R^3$, $R^4$, $R^5$, $R^6$, $R^8$, $R^9$ may be the same or different and are substituents, such as a hydrogen. X represents a halogen atom, and $R^7$ represents a substituent having 3 to 20 carbon atoms with a π bond. RS1 represents the main chain of the synthetic resin precursors having —$CH_2OH$ group at their end.

(Continued)

Measurement Result of Precursor of Organometallic complex Part (M9)

(P1)

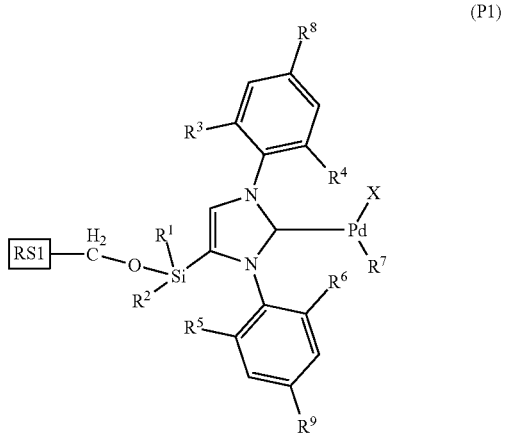

3 Claims, 16 Drawing Sheets

(56) References Cited

FOREIGN PATENT DOCUMENTS

WO 2018/105671 A1 6/2018
WO 2018/105672 A1 6/2018

OTHER PUBLICATIONS

International Search Report dated Dec. 3, 2019, issued in counterpart International Application PCT/JP2019/033649 (2 pages).
Wang, Yuzhong et al., "A Viable Anionic N-Heterocyclic Dicarbene", J. Am. CHem. Soc. Sep. 23, 2010, vol. 132, No. 41, pp. 14370-14372; Cited in ISR dated Dec. 3, 2019.
Mendoza-Espinosa, Daniel et al., "Synthesis of 4- and 4,5-Functionalized Imidazol-2-ylidenes from a Single 4,5-Unsubstituled Imidazol-2-ylidene", J. Am. Chem. Soc., May 5, 2010, vol. 132, No. 21, pp. 7264-7265; Cited in ISR dated Dec. 3, 2019.
Ansell, Melvyn B. et al., "Synthesis of an [(NHC}2Pd(SiMe3)2] Complex and Catalytic cis-Bis(silyl)ations of Alkynes with Unactivated Disilanes", Angew. Chem. Int. Ed., Apr. 9, 2015, vol. 54, No. 19, pp. 5578-5582; Cited in ISR dated Dec. 3, 2019.
Mohammadi, Elmira et al., "Synthesis of polystyrene-supported Pd(II)-NHC complex derived from theophylline as an efficient and reusable heterogeneous catalyst for the Heck-Matsuda cross-coupling reaction", Journal of Molecular Catalysis A Chemical, Apr. 1, 2016, vol. 418-419, pp. 158-167; Cited in ISR dated Dec. 3, 2019.

Kosugi, Masanori et al., "Palladium-Catalyzed Aromatic Amination of Aryl Bromides With N, N-Di-Ethylamino-Tributyltin", Chemistry Letters, 1983, pp. 927-928; Cited in the specification.
Guram, Anil S. et al., "A Simple Catalytic Method for the Conversion of Aryl Bromides to Arylamines", Angew. Chem., Int. Ed. Engl., 1995, vol. 34, No. 12, pp. 1348-1350; Cited in the Specification.
Louie, Janis et al., "Palladium-Catalyzed Synthesis of Arylamines from Aryl Halides, Mechanistic Studies Lead to Coupling in the Absence of Tin Reagents", Tetrahedron Letters, vol. 36, No. 21, 1995, pp. 3609-3612; Cited in the Specification.
Arduengo, Anthony J., et al., "A Stable Crystalline Carbene", American Chemical Society, 1991, 113, pp. 361-363; Cited in the Specification.
Organ, Michael G. et al., "Rational catalyst design and its application in sp3-sp3 couplings", Presented at the 230th National Meeting of the American Chemical Society, Washington, DC, 2005; Cited in the Specification.
Organ, Michael G. et al., "A User-Friendly, All-Purpose Pd-NHC (NHC=N-Heterocyclic Carbene) Precatalyst for the Negishi Reaction: A Step Towards a Universal Cross-Coupling Catalyst", Chem. Eur. J., 2006, 12, pp. 4749-4755; Cited in the specification.
Ray, Lipika et al., "Air-stable, convenient to handle Pd based PEPPSI (pyridine enhanced precatalyst preparation, stabilization and initiation) themed precatalysts of N/O-functionalized N-heterocyclic carbenes and its utility in Suzuki-Miyaura cross-coupling reaction", The Royal Society of Chemistry, Dalton Trans, 2007, pp. 4546-4555; Cited in the Specification.
O'Brien Christopher J. et al., "Easily Prepared Air- and Moisture-Stable Pd-NHC (NHC=N-Heterocyclic Carbene) Complexes: A Reliable, User-Friendly, Highly Active Palladium Precatalyst for the Suzuki-Miyaura Reaction", Chem. Eur. J. 2006, 12, pp. 4743-4748; Cited in the Specification.
Marion, Nicolas et al., "Modified (NHC)Pd(allyl)Cl (NHC = N-Heterocyclic Carbene) Complexes for Room-Temperature Suzuki-Miyaura and Buchwald-Hartwig Reactions", J. Am. Chem. Soc., 2006, 128, pp. 4101-4111; Cited in the Specification.
Navarro, Oscar et al., "Rapid Room Temperature Buchwald-Hartwig and Suzuki-Miyaura Couplings of Heteroaromatic Compounds Employing Low Catalyst Loadings", Chem. Eur. J. 2006, 12, pp. 5142-5148; Cited in the Specification.
Islam, Sk. Manirul et al., "Highly efficient recyclable polymer anchored palladium catalyst for C-C and C-N coupling reactions", Journal of Molecular Catalysis A: Chemical, 2013, 366, pp. 321-332: Cited in the Specification.
Parrish, Cynthia A et al., "Use of Polymer-Supported Dailkylphosphinobiphenyl Ligands for Palladium-Catalyzed Amination and Suzuki Reactions" J. Org. Chem. 2001, 66, pp. 3820-3827; Cited in the Specification.
Leyva, Antonio et al., "A soluble polyethyleneglycol-anchored phosphine as a highly active, reusable ligand for Pd-catalyzed couplings of arylchlorides: comparison with cross and non-crosslinked polystyrene and silica supports" Tetrahedron, 2007, 63, pp. 7097-7111; Cited in the specification.

* cited by examiner

Measurement Result of Precursor of Organometallic complex Part (M9)

Measurement Result of Precursor of Organometallic complex Part (M9)

Fig. 4

Measurement Result of Precursor of Organometallic complex Part (M9)

1H NMR (400 MHz, C$_6$D$_6$)
7.29 [s, 1H, NC*H*], 7.24-7.12 [m, 4H, Ar-*H*], 7.07-7.01 [m, 2H, Ar-*H*], 4.46-4.36 [m, 1H, CH$_2$C*H*=CH$_2$], 3.81 [dd, J=7.2 Hz, 1H, CH$_2$CH=CH$_2$], 3.42-3.32 [m, 2H, C*H*(CH$_3$)$_2$], 3.21 [m, 1H, C*H*(CH$_3$)$_2$], 3.05 [m, 1H, CH$_2$CH=C*H$_2$*], 2.99 [m, 1H, C*H*(CH$_3$)$_2$], 2.73 [d, J=13.4 Hz, 1H, C*H$_2$*CH=CH$_2$], 1.62 [d, J=12.1 Hz, 1H, C*H$_2$*CH=CH$_2$], 1.46-1.34 [m, 12H, CH(C*H$_3$*)$_2$], 1.14-1.00 [m, 12H, CH(C*H$_3$*)$_2$], 0.11 [d, J=7.4, 6H, Si(CH$_3$)$_2$]

13C{1H} NMR (100 MHz, C$_6$D$_6$)
191.2 [NCN], 146.7, 146.3, 146.0, 145.6, 136.6, 135.4, 132.8, 130.0, 129.8, 124.3, 124.2, 124.1, 123.6 [Ar-C], 113.6 [CH$_2$CH=CH$_2$], 72.3 [CH$_2$CH=CH$_2$], 50.0 [CH$_2$CH=CH$_2$], 28.7, 28.6, 28.3, 28.1, 26.1, 25.4, 25.2, 24.6, 24.5, 23.1, 22.6[CH(CH$_3$)$_2$], 2.4, 2.2 [d, J=10.0 Hz, Si(CH$_3$)$_2$]

29Si{1H} NMR (80 MHz, C$_6$D$_6$)
11.8

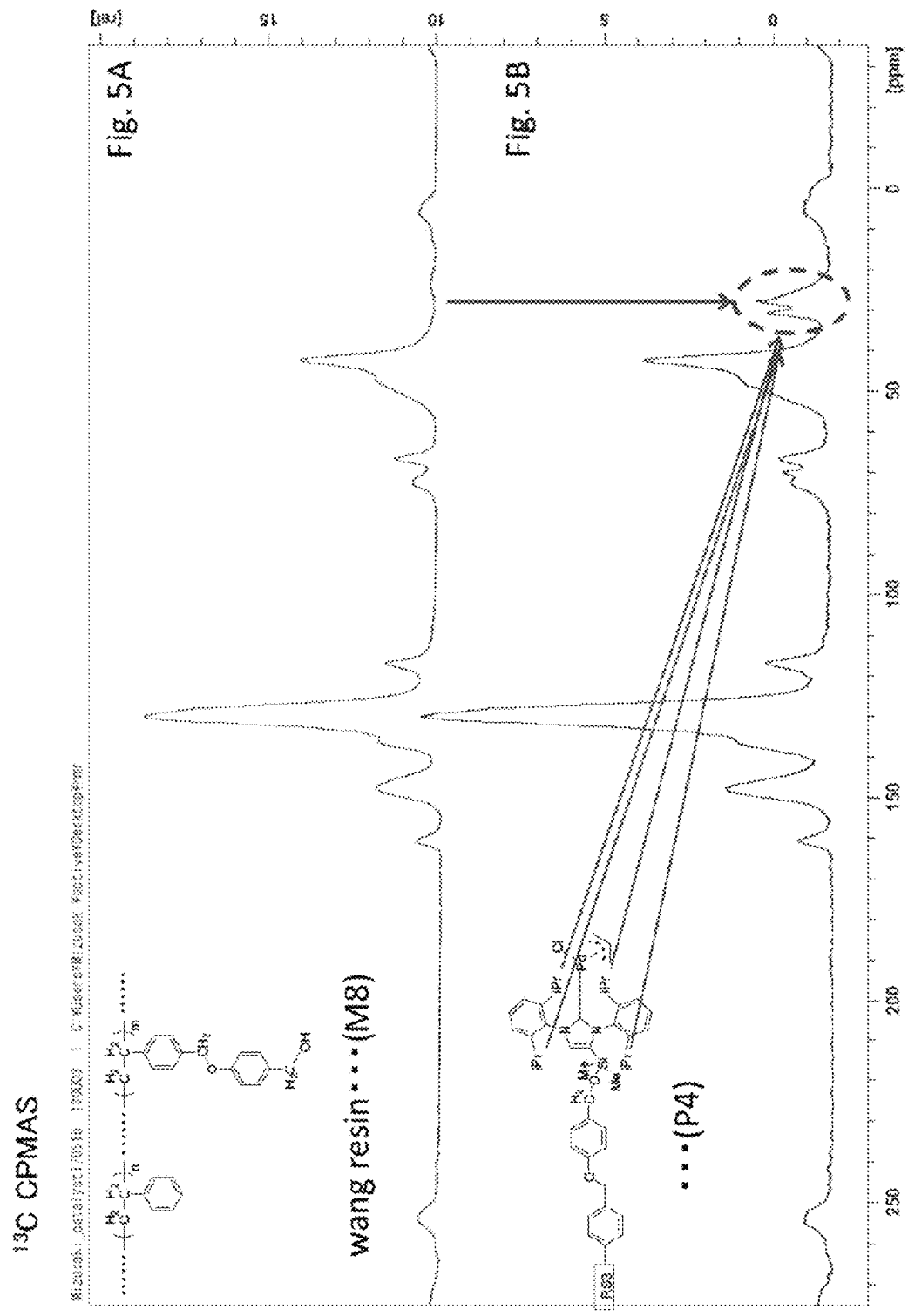

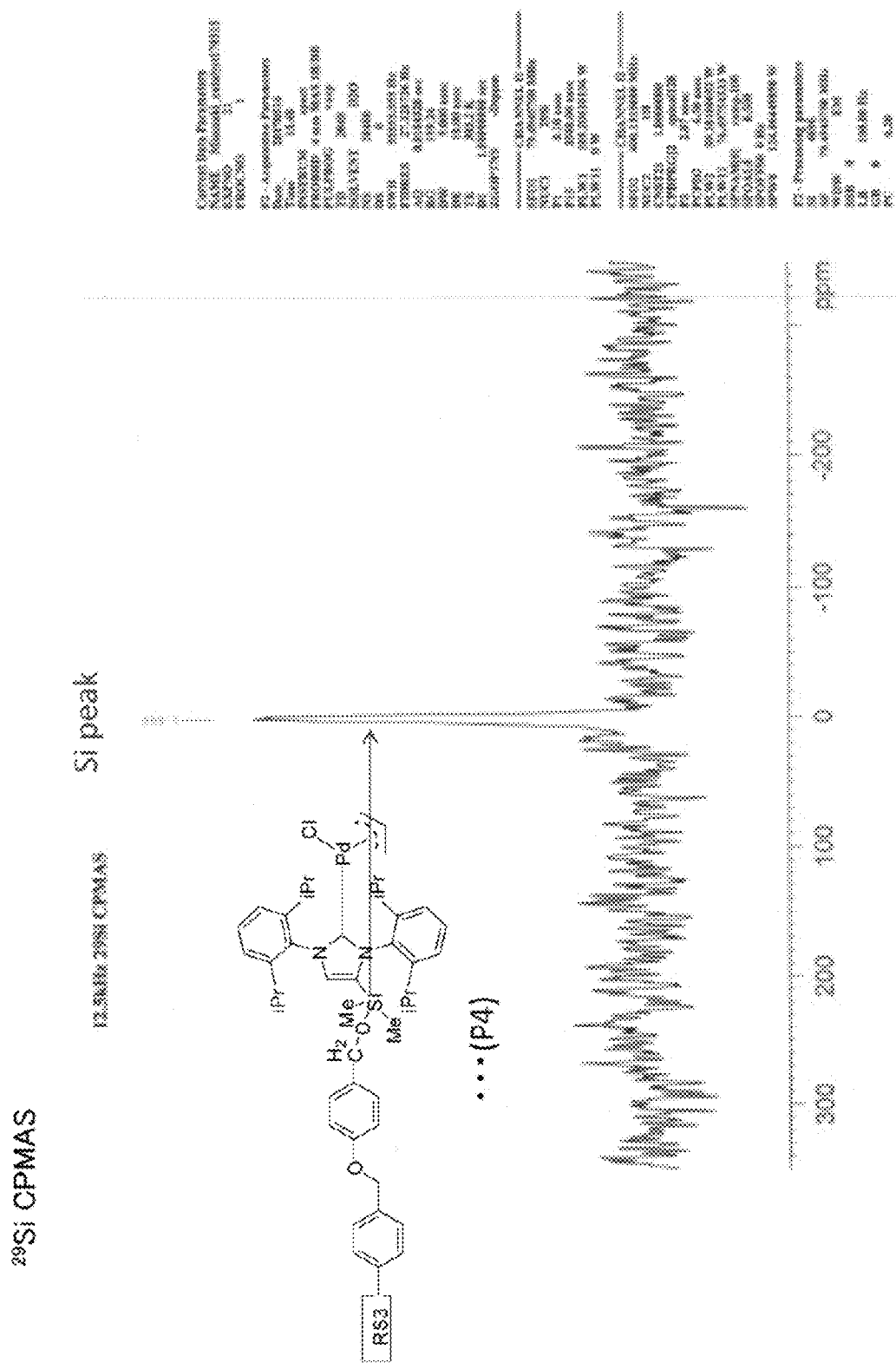

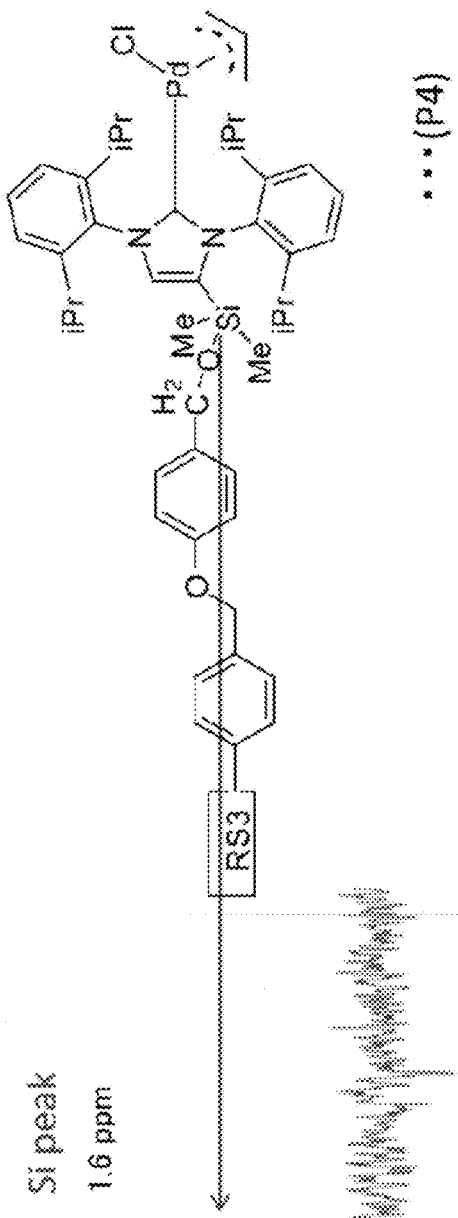
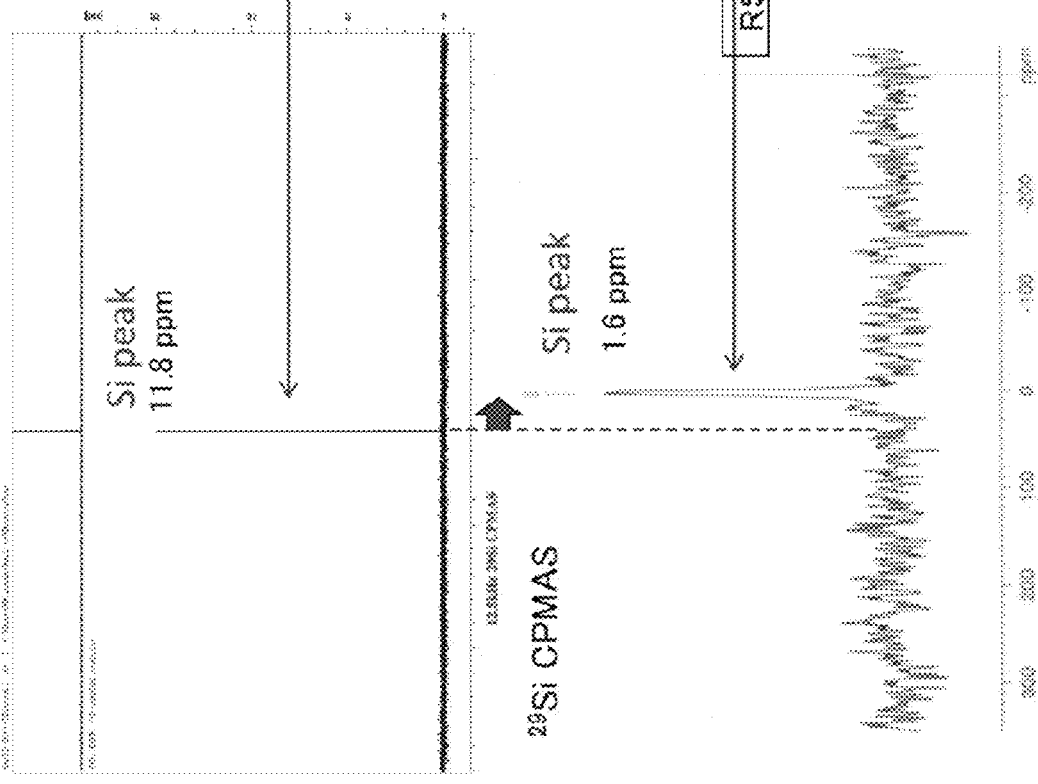
Fig. 7A ²⁹Si{¹H} NMR (C₆D₆) — Si peak 11.8 ppm — (M9)
Fig. 7B ²⁹Si CPMAS — Si peak 1.6 ppm — (P4)
Measurement Result of Catalyst for a Cross-coupling Reaction of Example 1 (P4)

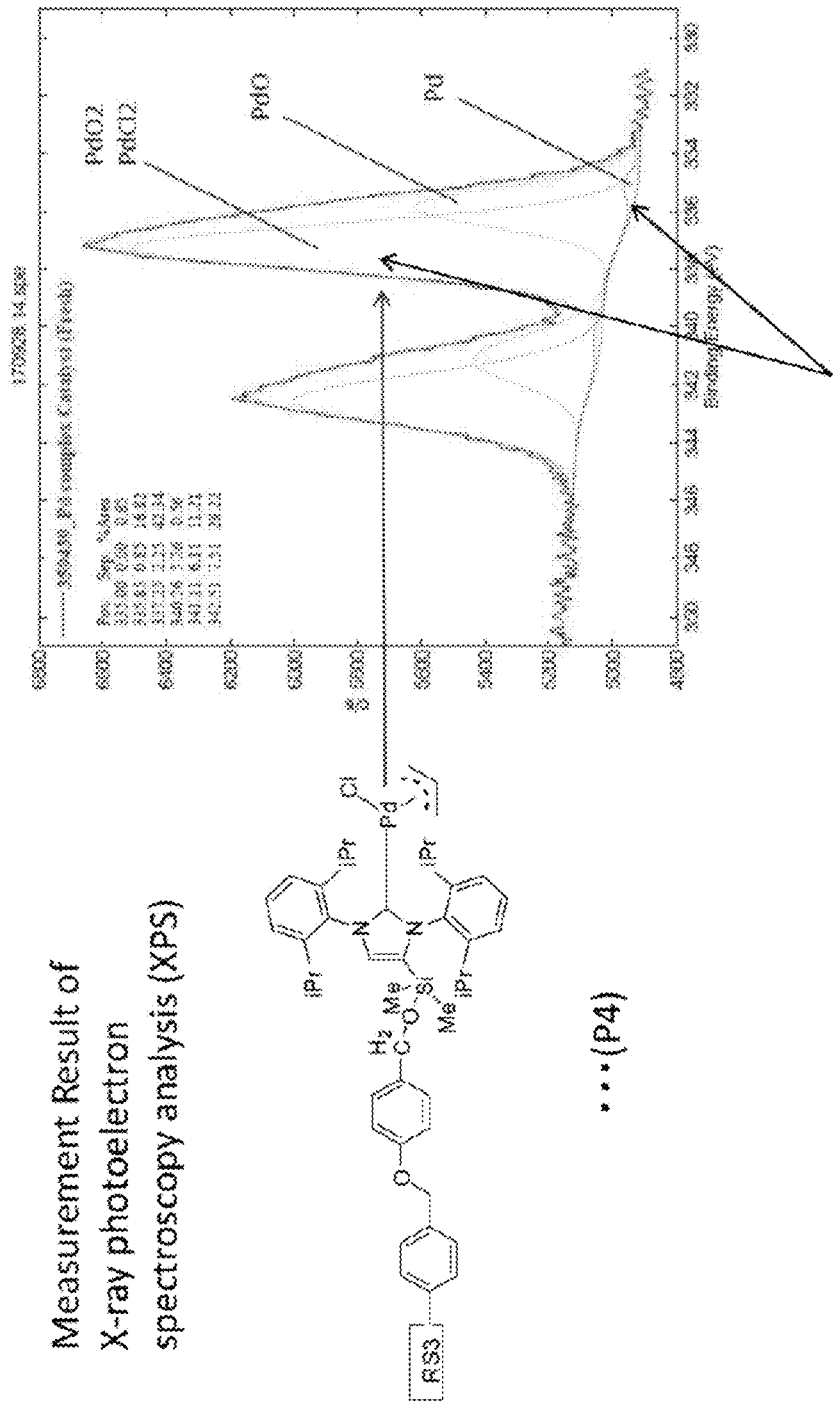

Fig. 16
Prior art summary about case wherein catalyst has organometallic complex with Pd coordination center immobilized on carrier such as synthesis resin, and case wherein organometallic complex with Pd coordination center and carrier such as synthesis resin are used for reaction (immobilization of complex on carrier is unclear)
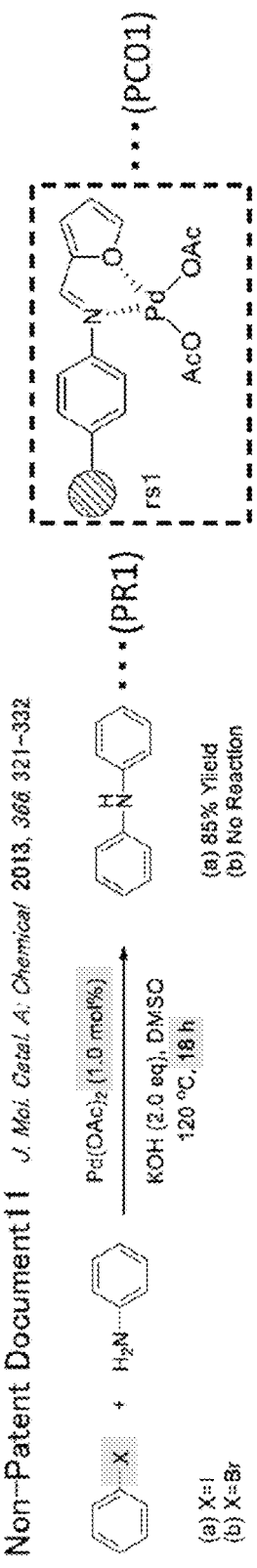
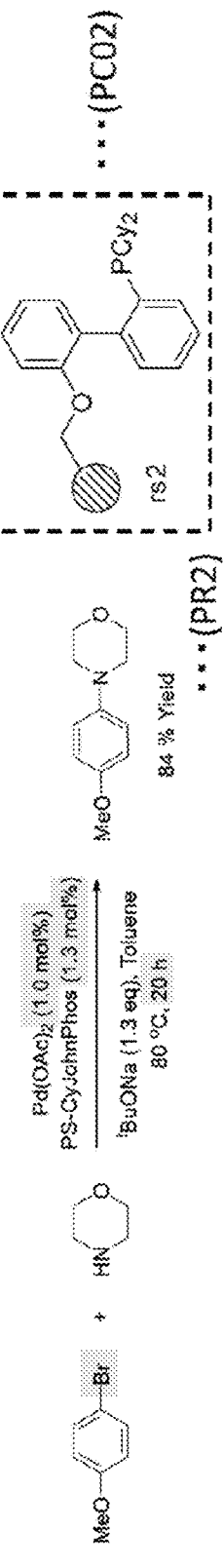
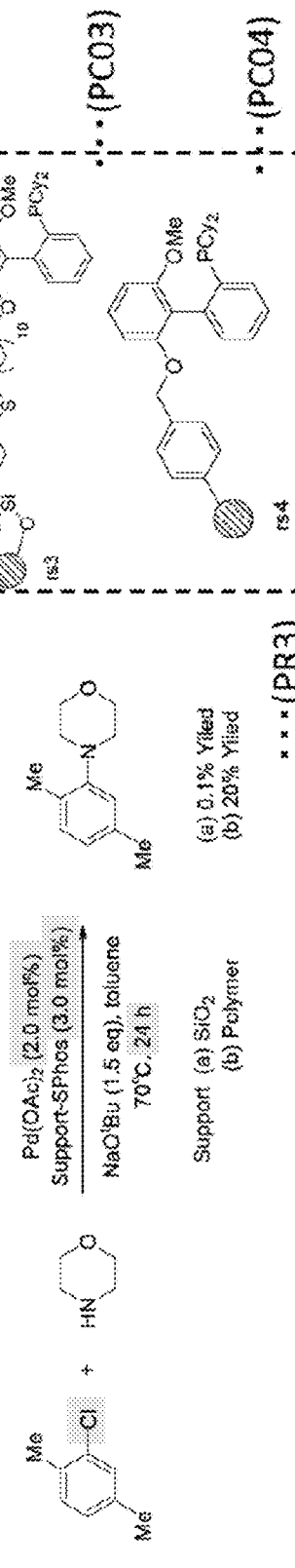

CROSS-COUPLING REACTION CATALYST

TECHNICAL FIELD

The present invention relates to a catalyst for a cross-coupling reaction. More particularly, the present invention relates to a catalyst for a cross-coupling reaction having a structure, in which an organometallic complex (precursor) having Pd serving as a coordination center and a ligand having a structure of a nitrogen-containing heterocyclic carbene is immobilized by chemical bonding on a synthetic resin (precursor) having a —$CH_2OH$ group at the end.

BACKGROUND ART

Aromatic amines are widely utilized in pharmaceutical, agrochemical, and electronic materials applications.

As a method for synthesizing this aromatic amine, there is reported a synthesizing method by a C—N coupling reaction using a palladium complex catalyst (for example, Non-Patent Documents 1 to 3).

Further, to proceed more efficiently this C—N coupling reaction, there is suggested a Pd-complex catalyst having a ligand having a structure of a nitrogen-containing heterocyclic carbene (N-Heterocyclic Carbene and, hereinafter, referred to as "NHC", if necessary).

The ligand containing the structure of this NHC was isolated for the first time as a crystalline NHC by Arduengo et al. in 1991, and its structure has been confirmed by X-ray crystal structure analysis (see, for example, Non-Patent Document 4 and the chemical formula (1) below).

[Chemical 1]

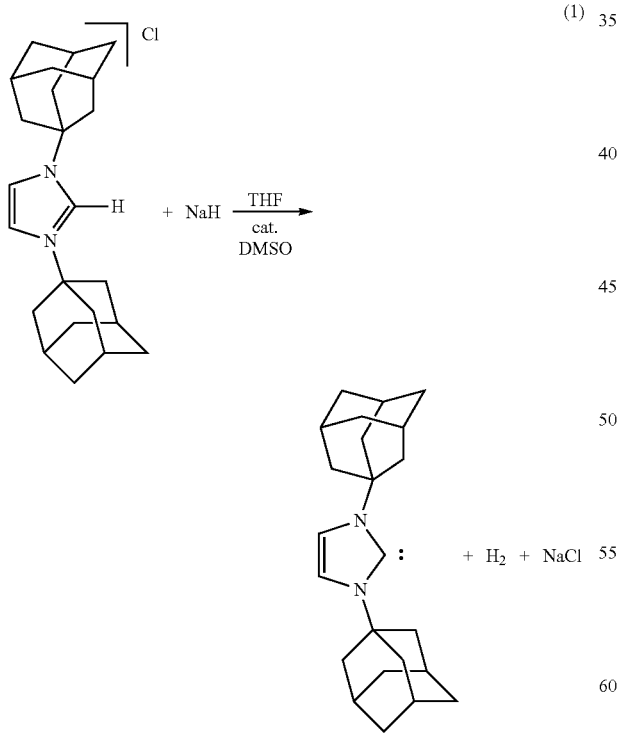

(1)

wherein, in the formula (1), cat. represents a predetermined catalyst, THF represents tetrahydrofuran, and DMSO represents dimethyl sulfoxide (Dimethyl sulfoxide).

It is known that a Pd complex catalyst having a ligand having this structure of NHC (hereinafter, referred to as "NHC—Pd complex catalyst", if necessary) has high coordination ability to palladium due to the strong a donor property of NHC and the weak n acceptor property, and is stable to air and water in the complex state. Also, a number of examples have been reported which have been used as catalysts for various cross-coupling reactions and exhibited very active properties.

As this NHC—Pd complex catalyst, for example, an NHC—Pd complex catalyst named "PEPPSI" has been proposed by Organ et al. in 2005 (for example, Non-Patent Document 5). This PEPPSI is useful as a coupling reaction catalyst and has been used in many reactions including Suzuki coupling reactions (see, for example, Non-Patent Documents 6 to 8 and the chemical formula (2) below).

[Chemical 2]

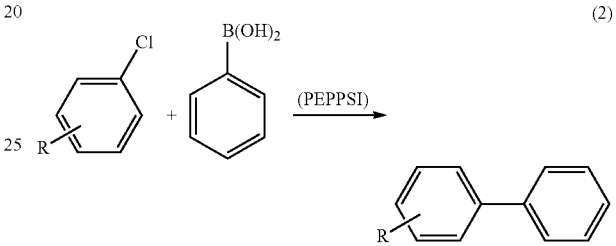

(2)

Herein the formula (2), R represents a hydrocarbon group (including a hydrocarbon group consisting of carbon and hydrogen, and a hydrocarbon group containing —$NH_2$ group, —SH group and —OH group), —$NH_2$ group, —SH group, and —OH group, and "PEPPSI" represents an abbreviation of Pyridine Enhanced Precatalyst Preparation Stabilization Initiation and has a chemical structure represented by the following formula (3).

[Chemical 3]

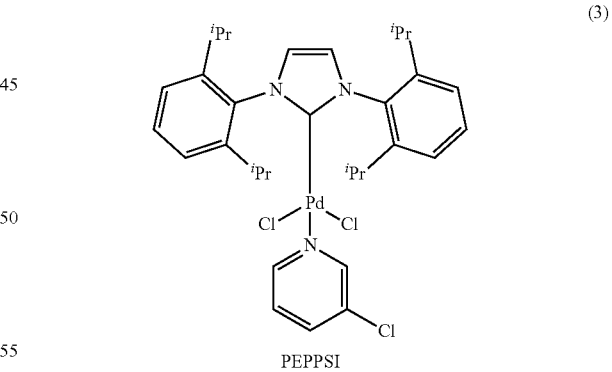

(3)

Herein, in the formula (3), "$^{i}Pr$" represents an isopropyl group (Isopropyl group).

In addition, various NHC—Pd complex catalysts were proposed by Nolan et al. in 2006. It has been reported, for example, that when an NHC—Pd complex catalyst ("IPrPd(allyl") represented by the following formula (4) is used as a catalyst for a C—N coupling reaction represented by the following formula (6), for example, the reaction proceeds well even at room temperature (see, for example, Non-Patent Documents 9 to 10).

[Chemical 4]

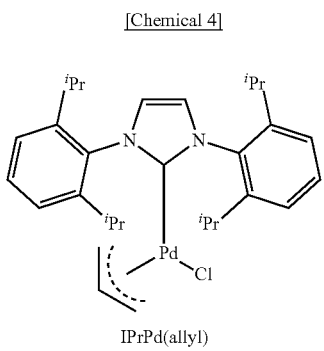

IPrPd(allyl)

(4)

Here, in this specification, "IPr" represents a ligand having an NHC structure represented by the following formula (5) (1,3-bis(2,6-diisopropylphenyl)imidazole-2-ylidene).

[Chemical 5]

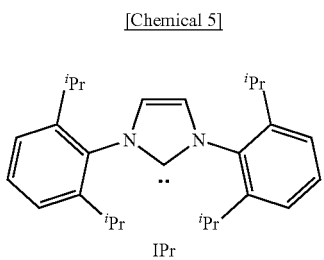

IPr (5)

[Chemical 6]

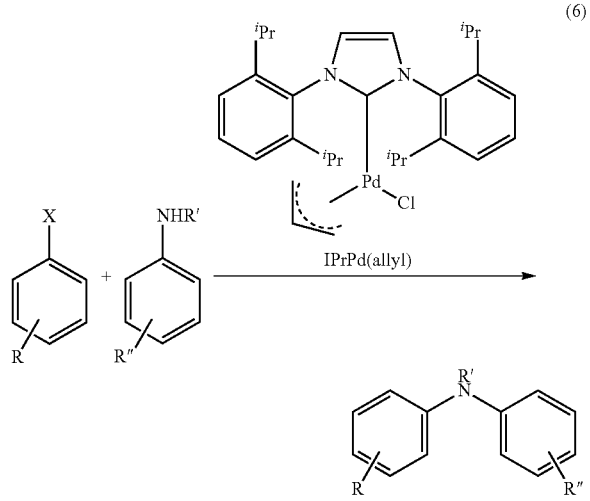

(6)

Here, in the formula (6), R, R', and R" may be the same or different from each other and represent a hydrocarbon group (including a hydrocarbon group consisting of carbon and hydrogen, and a hydrocarbon group including an NH$_2$ group, —SH group and —OH group), —NH$_2$ group, —SH group, and —OH group, and "'Bu" represents a tert-butyl group (tertiary butyl group).

Further, the present inventors have found that an organometallic complex catalyst having a structure, in which a substituent (silyl group) containing a silicon atom bonded to a carbon atom (backbone carbon) at the 4-position or the 5-position in the structure of NHC of an imidazole ring is bonded, is effective from the viewpoint of obtaining an object product of a cross-coupling reaction at a high yield (see Patent Document 1 and Patent Document 2).

On the other hand, in the cross-coupling reaction, the organometallic complex catalyst is often present in a state in which the organometallic complex catalyst is dissolved together with the product in the reaction solution after the reaction, and there is a problem that its separation from the product is not easy.

Therefore, attempts have been made to immobilize an organometallic complex catalyst on a carrier such as a synthetic resin. For example, Non-Patent Document 11 discloses a case of a catalyst in which an organometallic complex having a coordination center of Pd is immobilized on a polymer carrier. In addition, Non-Patent Document 12 and Non-Patent Document 13 disclose a case where an organometallic complex having a Pd coordination center is used for reactions together with a polymer carrier (or a carrier composed of SiO$_2$ powder).

Note that, in Non-Patent Document 12 and Non-Patent Document 13, it is not clearly confirmed whether or not an organometallic complex catalyst is immobilized on a carrier.

FIG. 16 is an explanatory view representing an outline of a catalyst described in Non-Patent Document 11, Non-Patent Document 12 and Non-Patent Document 13, respectively, and a cross-coupling reaction (C—N cross-coupling reaction) using the catalyst.

In Non-Patent Document 11, a catalyst having a structure represented by the formula (PC01) is used for a cross-coupling reaction represented by the formula (PR1). Note that, in the formula (PC01), "rs1" represents a polystyrene polymer. In addition, in the formula (PR1), "DMSO" represents dimethyl sulfoxide (Dimethyl sulfoxide). In both formulae, Ac represents —CH$_3$CO group. As shown in FIG. 16, it has been reported that when iodobenzene is used as a reactant (substrate), the reaction proceeds, but when bromobenzene is used, the reaction does not proceed.

In Non-Patent Document 12, a catalyst having a structure represented by the formula (PC02) is used for a cross-coupling reaction represented by the formula (PR2). Note that, in the formula (PC02), "rs2" represents Merrifield Resin (chloromethyl polystyrene resin).

In addition, in the formula (PR2), "PS" represents polystyrene, and "CyJohnPhos" represents (2-biphenyl) dicyclohexylphosphine. In addition, in the formula (PR2), "'Bu" represents a tert-butyl group (tertiary butyl group) and "Me" represents a methyl group. As shown in FIG. 16, it has been reported that the reaction proceeds when a 4-bromoanisole in which a hydrogen at the para-position of the benzene ring of anisole is substituted with Br is used as a reactant (substrate).

In Non-Patent Document 13, a catalyst having a structure represented by the formula (PC03) or a catalyst having a structure represented by the formula (PC04) is used for a cross-coupling reaction represented by the formula (PR3). Incidentally, in the formula (PC03), "rs3" represents SiO$_2$ powder. In addition, in the formula (PC04), "rs4" represents Merrifield Resin (chloromethyl polystyrene resin). In addition, in the formula (PC03) and the formula (PC04), "PCy2" represents a dicyclohexylphosphine group. And, in the formula (PR3), "SPhos" represents 2-Dicyclohexylphosphino-2', 6'-dimethoxybiphenyl. As shown in FIG. 16, it has been reported that when 1,4-dimethyl-2-chlorobenzene is used as a reactant (substrate), the reaction proceeds only slightly with the catalyst containing SiO$_2$ powder as the carrier, but the reaction proceeds more with the catalyst containing the synthetic resin as the carrier. It has also been reported that adding and mixing 7 times SPhos to the Pd(OAc)$_2$ improves the yield of the product to about 90%.

The applicant of the instant patent application presents the following publications as publications in which the known inventions described in the above publications are described.

PRIOR ART DOCUMENT

Non-Patent Document

Non-Patent Document 1: Kosugi, M., Kameyama, M., Migita. T. Chem. Lett. 1983, 927
Non-Patent Document 2: Guram, A. S., Rennels, R. A., Buchwald, S. L. Angew. Chem., Int. Ed. Engl. 1995, 34, 1348
Non-Patent Document 3: Louie, J., Hartwig, J. F. Tetrahedron Lett. 1995, 36(21), 3609
Non-Patent Document 4: Louie, J., Arduengo, A. J. Am. Chem. Soc. 1991, 113, 361
Non-Patent Document 5: Organ, M. G. Rational catalyst design and its application in sp$^3$-sp$^3$ couplings. Presented at the 230th National Meeting of the American Chemical Society, Washington, D C, 2005; Abstract 308.
Non-Patent Document 6: Organ, M. G., Avola, S., Dubovyk, L., Hadei, N., Kantchev, E. A. B., OBrien, C., Valente, C. Chem. Eur. J. 2006, 12, 4749
Non-Patent Document 7: Ray, L., Shaikh, M. M., Ghosh, P. Dalton trans. 2007, 454
Non-Patent Document 8: Obrien, C. J., Kantchev, E. A. B., Valente, C., Hadei, N., Chass, G. A., Lough, A., Hopkinson, A. C., Organ, M. G. Chem. Eur. J. 2006, 12, 4743
Non-Patent Document 9: Marion, M., Navarro, O., Stevens, J. M, E., Scott, N. M., Nolan, S. P. J. Am. Chem. Soc. 2006, 128, 4101
Non-Patent Document 10: Navarro, O., Marion, N., Mei, J., Nolan, S. P.Chem. Eur. J. 2006, 12, 5142
Non-Patent Document 11: Sk. Manirul Islam, Noor Salam, Paramita Mondal, Anupam Singha Roy, J. Mol. Catal. A: Chemical 2013, 366, 321-332 Non-Patent Document 12: Cynthia A. Parrish, Stephen L. Buchwald, J. Org. Chem. 2001, 66, 3820-3827
Non-Patent Document 13: Antonio Leyva, Hermenegildo Garcia, Avelino Corma, Tetrahedron 2007, 63, 7097-7111

Patent Document

Patent Document 1: WO2018/105671
Patent Document 2: WO2018/105672

SUMMARY OF THE INVENTION

Problem to be Solved by the Invention

However, the present inventors have found that, in a cross-coupling reaction using a catalyst for a cross-coupling reaction in which an organometallic complex is immobilized onto a carrier, there is still room for improvement even in the above-described catalyst of the prior art from the viewpoint of obtaining a high yield of an object product in a relatively small amount of catalyst used and a relatively short time.

Particularly in a C—N cross-coupling reaction, a compound having a C—X bond (X represents halogen atom) such as a benzene halide (and a derivative thereof) serving as a precursor (substrate) on the "C" side of the C—N bond can greatly reduce the raw material cost of the precursor (substrate) when the halogen of the substituent can be changed from I to Br and further from Br to Cl. For example, changing from Br to Cl may result in about half the raw material cost.

In the prior art described above, a case has been reported in which a 1,4-dimethyl-2-chlorobenzene is used as a reactant (substrate) in the prior art document 13, but the present inventors believe that the amount of the catalyst used is relatively large and the reaction time is relatively long and there is room for improvement, and further, there is room for improvement in the yield of the object product. In addition, in non-patent document 13, an organometallic complex catalyst (Pd(OAc))$_2$) and a carrier (SPhos) are mixed into the reaction solution, but whether the organometallic complex catalyst (Pd(OAc))$_2$) is immobilized on the carrier (SPhos) has not been clearly confirmed. If the organometallic complex catalyst (Pd(OAc)$_2$) is not sufficiently immobilized on the carrier (SPhos), the catalyst and the product cannot be easily separated from the reaction solution.

The present invention was completed in view of such technical circumstances and it is an object of the present invention to provide a catalyst for a cross-coupling reaction in which an organometallic complex is sufficiently immobilized on a carrier, and an object product can be easily obtained in a high yield and in a relatively short reaction time with a relatively small amount of use.

Means to Solve the Problems

The present inventors have found so far, as an organometallic complex catalyst highly active in a cross-coupling reaction, an organometallic complex catalyst having a structure in which a substituent (silyl group) containing a silicon atom bonded to a carbon atom at the 4-position or the 5-position (hereinafter, referred to as "backbone carbon", if necessary) in the structure of an NHC of an imidazole ring is bonded (see Patent Document 1 and Patent Document 2).

Further, the present inventors have researched a carrier capable of immobilizing an organometallic complex based on this organometallic complex catalyst, and intensively studied towards the solution of the above-mentioned problems such as performing the improvement of the organometallic complex for immobilization.

As a result, the present inventors have found that a catalyst for a cross-coupling reaction having a structure of the following formula (P1) is effective for solving the above problems and have completed the present invention.

More specifically, the present invention is composed of the following technical matters.

That is, the present invention provides,
a catalyst for a cross-coupling reaction used in a cross-coupling reaction comprising;
a carrier part composed of a synthetic resin,
an organometallic complex part immobilized on the carrier part by chemical bonding,
wherein
the coordination center of the organometallic complex is Pd,
the organometallic complex of the precursor of the organometallic complex part has a structure represented by the following formula (M1),
the synthetic resin precursor of the precursor of the carrier part has a structure represented by the following formula (M2), the catalyst having a structure represented by the following formula (P1) corresponding to a product of a condensation reaction represented by the following formula (M3) in which the organometallic complex and the synthetic resin precursor are used as reactants.

[Chemical 7]

(P1)

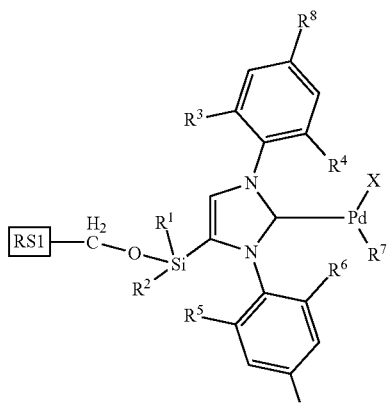

[Chemical 8]

(M1)

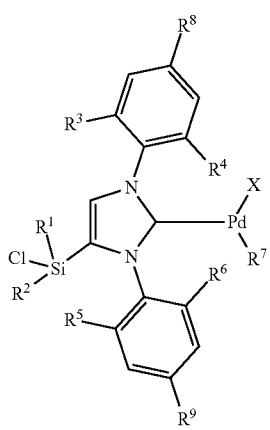

[Chemical 9]

(M2)

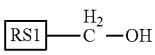

[Chemical 10]

(M3)

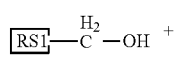 +

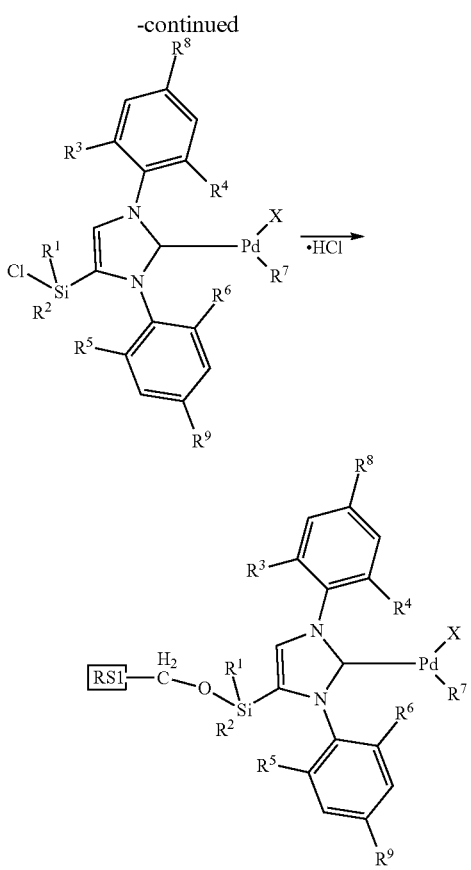

Here, in the formula (P1), $R^1$ and $R^2$ may be the same or different and are, respectively, at least one substituent selected from the group consisting of hydrogen atom, alkyl group, alkoxy group, alkenyl group, alkynyl group, and aryl group.

$R^3$, $R^4$, $R^5$, $R^6$, $R^8$, and $R^9$ may be the same or different and are, respectively, at least one substituent selected from the group consisting of hydrogen atom, halogen atom, alkyl group, alkoxy group, alkenyl group, alkynyl group, aryl group, hydroxy group, hydroxylate group, thiocarboxy group, dithiocarboxy group, sulfo group, sulfino group, oxycarbonyl group, carbamoyl group, hydradinocarbonyl group, amidino group, cyano group, isocyano group, cyanato group, isocyanato group, thiocyanato group. isothiocyanato group, formyl group, oxo group, thioformyl group, thioxo group, mercapto group, amino group, imino group, hydradino group, allyloxy group, sulfide group, nitro group, and silyl group.

X and $R^7$ may be the same or different and are, respectively, halogen atom coordinatable to Pd of the coordination center, a substituent having carbon number of 3 to 20 with a π bond coordinatable to Pd of the coordination center, or, a ligand selected from amine compound, phosphine compound, nitrile compound, sulfur compound or isocyanide compound.

RS1 represents the main chain of the synthetic resin precursor having a —$CH_2OH$ group at the end represented by the above formula (M2).

In the formula (M1) and the formula (M3), X, $R^1$, $R^2$, $R^3$, $R^4$, $R^5$, $R^6$, and $R^7$, $R^8$ and $R^9$, represent the same substituents as X, $R^1$, $R^2$, $R^3$, $R^4$, $R^5$, $R^6$, and $R^7$, $R^8$ and $R^9$ in the formula (P1).

In the formula (M3), RS1 represents the same main chain of the synthetic resin precursor as RS1 in the formula (P1).

The catalyst for a cross-coupling reaction of the present invention having the above-described constitution can easily give an object product at a high yield and in a relatively short reaction time with a relatively small amount of use in a cross-coupling reaction.

In addition, in the present invention, from the viewpoint of more reliably obtaining the effect of the present invention, it is preferable that X represents a halogen atom capable of coordinating to Pd of the coordination center in the formula (P1), the formula (M1), and the formula (M3).

Further, in the present invention, from the viewpoint of obtaining the effect of the present invention more reliably, it is preferable that $R^7$ represents a substituent having a carbon number of 3 to 20 with a π bond coordinatable to the Pd of the coordination center in the formula (P1), the formula (M1), and the formula (M3).

Although the detailed mechanism by which the catalyst for a cross-coupling reaction of the present invention can give an object product at a high yield has not been elucidated, the present inventors infer as follows.

First, the organometallic complex of the precursor of the organometallic complex part of the catalyst for a cross-coupling reaction in accordance with the present invention has a structure in which a silyl group (—$SiR^1R^2Cl$) is bonded to the backbone carbon at the 4-position or the 5-position in the structure of the NHC as shown in the formula (M1), and it is considered that the structure as it is exhibits high activity in a cross-coupling reaction as an organometallic complex catalyst.

Actually, the present inventors have confirmed in Patent Documents 1 and 2 that an organometallic complex having a structure in which Cl of the silyl group of the organometallic complex represented by the formula (M1) is replaced with a substituent having the same chemical composition as that of $R^1$ has a high activity as a catalyst for a cross-coupling reaction. In the present invention, in order to immobilize on the synthetic resin precursor (formula (M2)) serving as the precursor of the carrier part, the organometallic complex has been improved in which one of 3 substituents of a silyl group of the organometallic complex catalyst described in Patent Document 1 and Patent Document 2 is changed to Cl.

Then, in the condensation reaction in which Cl of the silyl group of the organometallic complex of the precursor represented by the formula (M1) and H of the —OH of —$CH_2$—OH group at the end of the synthetic resin precursor represented by the formula (M2) are removed as HCl, it is inferred that, even after the organometallic complex of the precursor becomes a form after being immobilized on the carrier part at the part of the silyl group, it has almost the same catalytic activity as that of the organometallic complex of the precursor, thereby contributing to improvement in the yield of the object product.

Effect of the Invention

In accordance with the present invention, there is provided a catalyst for a cross-coupling reaction, in which an organometallic complex is sufficiently immobilized on a carrier, and an object product can be easily obtained in a high yield and in a relatively short reaction time with a relatively small amount of use.

BRIEF DESCRIPTION OF THE DRAWINGS

FIG. 4 is an explanatory view representing the result of measuring $^1$H NMR spectrum of the spectrum shown in FIG. 1, the result of measuring $^{13}${H}NMR spectrum shown in FIG. 2, and the result of measuring the $^{29}$Si{$^1$H}NMR spectrum shown in FIG. 3.

FIG. 5 shows a graph representing $^{13}$C CPMAS spectrum obtained for Wang resin (FIG. 5A) and a graph representing the $^{13}$C CPMAS spectrum obtained for the catalyst for a cross-coupling reaction in Example 1 (FIG. 5B).

FIG. 6 is a graph representing the $^{29}$Si CPMAS spectrum obtained for the catalyst for cross-coupling reaction in Example 1.

FIG. 7A and FIG. 7B are a graph representing a $^{29}$Si{$^1$H}NMR spectrum (FIG. 7A) obtained for the precursor of the organometallic complex part and a $^{29}$Si CPMAS spectrum (FIG. 7B) obtained for the catalyst for a cross-coupling reaction of Example 1.

FIG. 8 is a graph representing the measurement result of X-ray photoelectron spectroscopy analysis (XPS) obtained for the catalyst for a cross-coupling reaction of Example 1.

FIG. 16 is an explanatory view representing the catalysts described in Non-Patent Document 11, Non-Patent Document 12 and Non-Patent Document 13, respectively, and an outline of the cross-coupling reaction (C—N cross-coupling reaction) using these catalysts.

MODE FOR CARRYING OUT THE INVENTION

Figure 1:
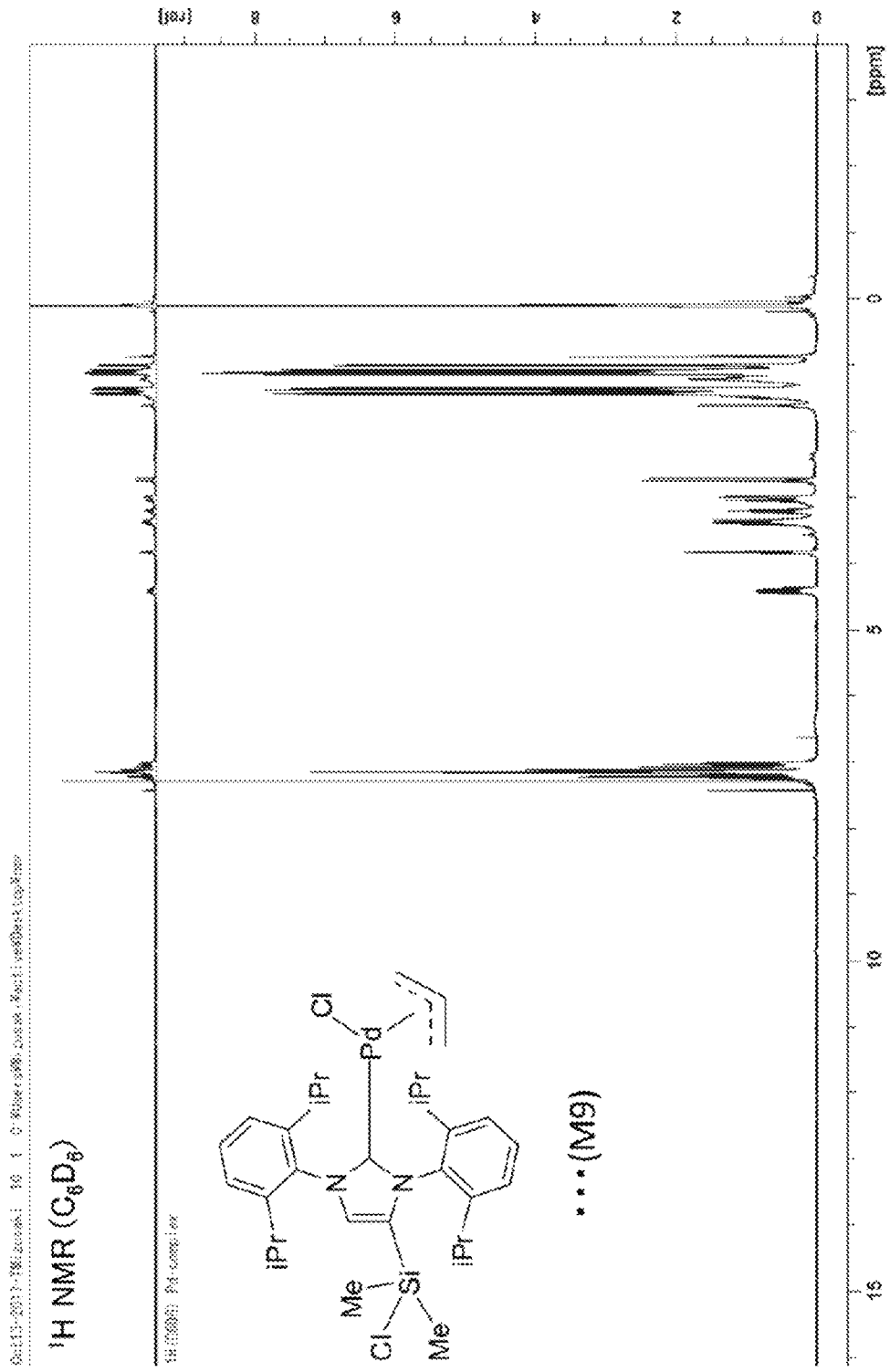
FIG. 1 is a graph representing $^1$H NMR spectrum obtained for the organometallic complex as a precursor (raw material) of the organometallic complex part of the cross-coupling reaction catalyst of Example 1 (the organometallic complex shown by the formula (M9)).

Hereinafter, preferred embodiments of the present invention will be described in detail.

<Constitution of a Catalyst for a Cross-Coupling Reaction>

The catalyst for a cross-coupling reaction in accordance with this embodiment is an organometallic complex catalyst used in a cross-coupling reaction, preferably a C—N cross-coupling reaction, has a carrier part composed of a synthetic resin and an organometallic complex part immobilized on this carrier part by chemical bonding, in which the coordination center of the organometallic complex part is Pd, and the catalyst has a structure represented by the following formula (P1).

[Chemical 11]

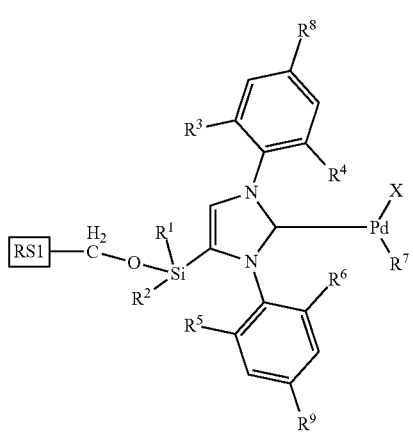

(P1)

Further, the organometallic complex serving as a precursor of the organometallic complex part has a structure represented by the following formula (M).

Further, the synthetic resin precursor of the precursor of the carrier part has a structure represented by the following formula (M2).

Then, the structure represented by the formula (P1) corresponds to the structure of the product of the condensation reaction represented by the following formula (M3) using the organometallic complex and the synthetic resin precursor as the reactants.

[Chemical 12]

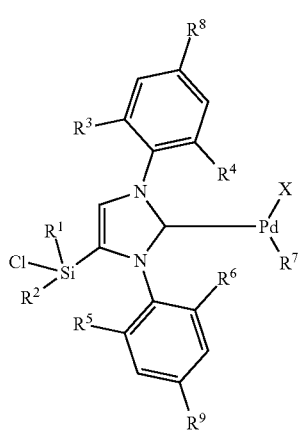

(M1)

[Chemical 13]

(M2)

[Chemical 14]

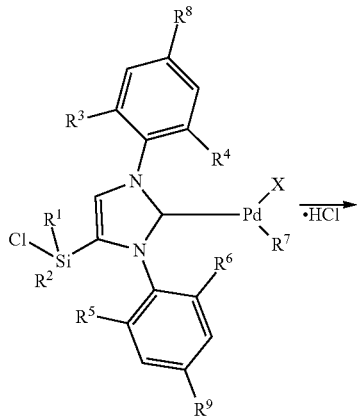

(M3)

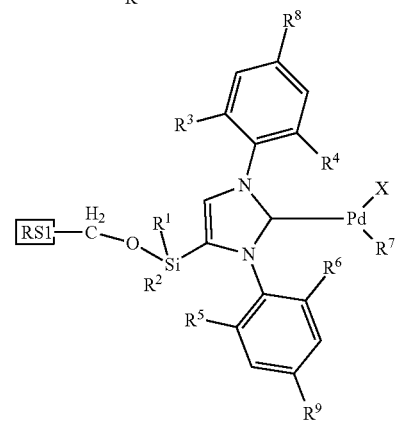

Here, in the formula (P1), $R^1$ and $R^2$ may be the same or different and are, respectively, at least one substituent selected from the group consisting of hydrogen atom, alkyl group, alkoxy group, alkenyl group, alkynyl group, and aryl group.

$R^3$, $R^4$, $R^5$, $R^6$, $R^8$ and $R^9$ may be the same or different and are, respectively, at least one substituent selected from the group consisting of hydrogen atom, halogen atom, alkyl group, alkoxy group, alkenyl group, alkynyl group, aryl group, hydroxy group, hydroxylate group, thiocarboxy group, dithiocarboxy group, sulfo group, sulfino group, oxycarbonyl group, carbamoyl group, hydradinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydradino group, allyloxy group, sulfide group, nitro group, and silyl group.

For example, the aryl group may be a 2,4,6, trimethylphenyl group.

X and $R^7$ may be the same or different and are, respectively, halogen atom coordinatable to Pd of the coordination center, a substituent having carbon number of 3 to 20 with a π bond coordinatable to Pd of the coordination center, or, a ligand selected from amine compound, phosphine compound, nitrile compound, sulfur compound or isocyanide compound.

RS1 represents the main chain of the synthetic resin precursor having —CH$_2$OH group at the end of the synthetic resin precursor represented by the formula (M2).

In the formula (M1) and the formula (M3), X, $R^1$, $R^2$, $R^3$, $R^4$, $R^5$, $R^6$, $R^7$, $R^8$ and $R^9$ represents the same substituent as X, $R^1$, $R^2$, $R^3$, $R^4$, $R^5$, $R^6$, $R^7$, $R^8$ and $R^9$ in the formula (P1).

In the formula (M3), RS1 represents the same main chain of the synthetic resin precursor as RS1 in the formula (P1).

The catalyst for a cross-coupling reaction of the present invention having the above-described constitution can easily obtain an object in a high yield and in a relatively short reaction time with a relatively small amount of use in a cross-coupling reaction.

Although the detailed mechanism by which the catalyst for a cross-coupling reaction of the present invention can give a high yield of an object product has not been elucidated, the present inventors infer as follows. First, the organometallic complex of the precursor of the organometallic complex part of the catalyst for a cross-coupling reaction in accordance with the present invention has a structure in which a silyl group (—SiR$^1$R$^2$Cl) is bonded to the backbone carbon at the 4-position or the 5-position in the structure of the NHC as shown in the formula (M1), and it is considered that the structure as it is exhibits high activity in the cross-coupling reaction as an organometallic complex catalyst.

Actually, the present inventors have confirmed in Patent Documents 1 and 2 that an organometallic complex having a structure in which Cl of the silyl group of the organometallic complex represented by the formula (M1) is replaced with a substituent having the same chemical composition as that of $R^1$ has a high activity as a catalyst for a cross-coupling reaction. In the present invention, in order to immobilize on the synthetic resin precursor (formula (M2)) serving as a precursor of the carrier part, an organometallic complex has been improved in which one of 3 substituents of the silyl group of the organometallic complex catalyst described in Patent Document 1 and Patent Document 2 is changed to Cl.

Then, in the condensation reaction in which Cl of the silyl group of the organometallic complex of the precursor shown in the formula (M1) and H of the —OH group of the —CH$_2$—OH group at the end of the synthetic resin precursor shown in the formula (M2) are removed as HCl, it is inferred that, even after the organometallic complex of the precursor becomes a form after being immobilized on the carrier part at the part of the silyl group, it has almost the same catalytic activity as that of the organometallic complex of the precursor, thereby contributing to improvement in the yield of the object product.

In addition, from the viewpoint of more reliably obtaining the effect of the present invention, it is preferable that the catalyst for a cross-coupling reaction of the present invention further has a structure represented by the formula (P2).

[Chemical 15]

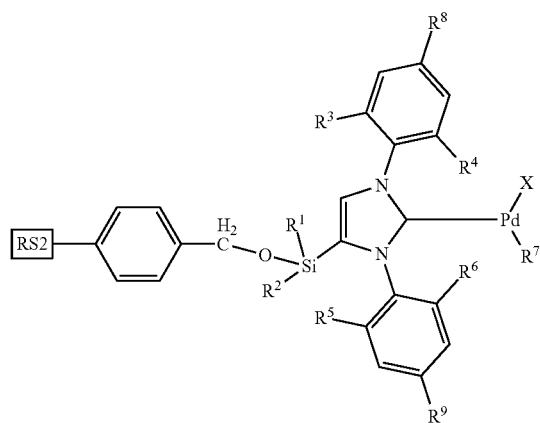

(P2)

In the formula (P2), X, $R^1$, $R^2$, $R^3$, $R^4$, $R^5$, $R^8$, $R^7$, $R^8$ and $R^4$ represent the same substituent as X, $R^1$, $R^2$, $R^3$, $R^4$, $R^5$, $R^6$, $R^7$, $R^8$ and $R^9$ in the formula (P1). In addition, RS2 represents the same main chain of the synthetic resin precursor as RS1 in the formula (P1).

Further, from the viewpoint of more reliably obtaining the effect of the present invention, it is preferable that the catalyst for a cross-coupling reaction of the present invention further has a structure represented by the following formula (P3).

[Chemical 16]

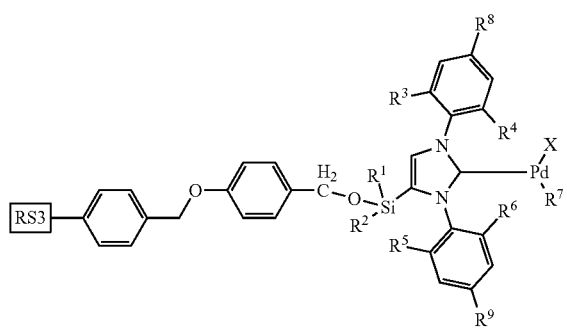

(P3)

Here, in the formula (P3), X, $R^1$, $R^2$, $R^3$, $R^4$, $R^5$, $R^6$, $R^7$, $R^8$ and $R^9$ represent the same substituent as X, $R^1$, $R^2$, $R^3$, $R^4$, $R^5$, $R^6$, $R^7$, $R^8$ and $R^9$ in the formula (P1). In addition, RS3 represents the same main chain of the synthetic resin precursor as RS1 in the formula (P1).

As a more preferable structure of the catalyst for a cross-coupling reaction having the structure of the formula (P3), a structure represented by the following formula (P4) can be mentioned.

[Chemical 17]

(P4)

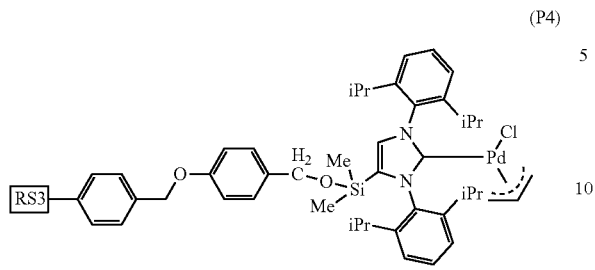

In the formula (P4), Pr represents an isopropyl group, and Me represents a methyl group.

At least one of $R^1$ and $R^2$ is preferably an alkyl group or an alkoxy group from the viewpoint of more reliably obtaining the effects of the present invention. More preferably, it is an alkyl group or an alkoxy group having a carbon number of 1 to 3.

It is preferable that at least one of $R^3$, $R^4$, $R^5$, $R^6$, $R^8$ and $R^9$ is an alkyl group having a carbon number of 1 to 3 from the viewpoint of obtaining the effect of the present invention more reliably.

In addition, in the present invention, from the viewpoint of more reliably obtaining the effect of the present invention, it is preferable that X represents a halogen atom capable of coordinating to Pd of the coordination center.

In addition, from the viewpoint of more reliably obtaining the effect of the present invention and from the viewpoint of availability of raw material and cost of raw material, it is more preferable that X is Cl among halogen atoms.

In the present invention, from the viewpoint of more reliably obtaining the effects of the present invention, it is preferable that $R^7$ represents a substituent having a carbon number of 3 to 20 with a π bond capable of coordinating to Pd of the coordination center.

Further, from the viewpoint of more reliably obtaining the effect of the present invention, $R^7$ is more preferably a substituent having a carbon number of 3 to 10 with a π bond possible of coordinating to Pd of the coordination center, and still more preferably a substituent having a carbon number of 3 to 9.

In addition, from the viewpoint of more reliably obtaining the effect of the present invention, it is preferable that the catalyst for a cross-coupling reaction of the present invention is used for a C—N cross-coupling reaction.

Further, from the viewpoint of more reliably obtaining the catalysts for a cross-coupling reaction having a structure of the formula (P2), the formula (P3), and the formula (P4), the synthetic resin precursor of the precursor of the carrier part represented by the formula (M2) preferably has a structure of the following formula (M4), and more preferably has a structure of the following formula (M5).

[Chemical 18]

(M4)

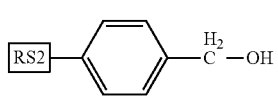

[Chemical 19]

(M5)

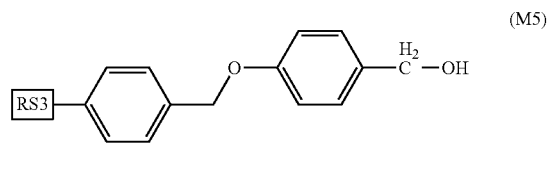

Here, RS2 in the formula (M4) and RS3 in the formula (M5) each represents the same main chain of the synthesize resin precursors as RS1 in the formula (P1).

Further, it is preferable that RS3 (or RS2, RS1) of the carrier part has a repeating unit represented by the following formula (M6) and a repeating unit represented by the following formula (M7).

[Chemical 20]

(M6)

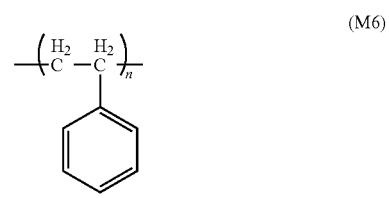

[Chemical 21]

(M7)

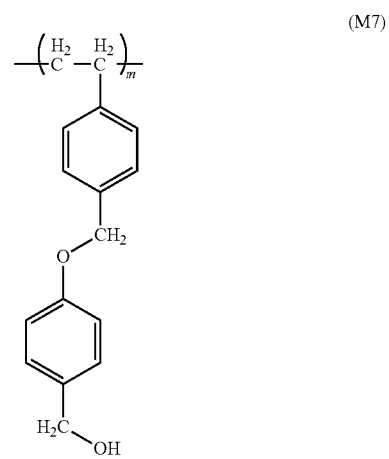

Here, in the formula (M6), n is an integer of 1 or more. In the formula (M7), m is an integer of 1 or more.

Further, RS3 (or RS2, RS1) of the carrier part may have a structure in which the repeating unit represented by the formula (M6) and the repeating unit represented by the formula (M7) are combined in any number and in any combination. For example, it may have a structure represented by the following formula (M8).

[Chemical 22]

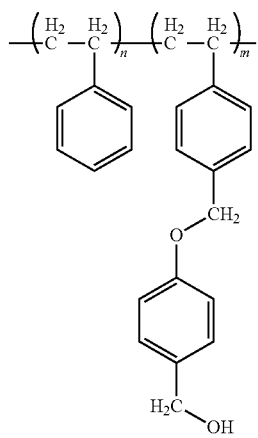

(M8)

As a preferable specific example of the synthetic resin precursor of the precursor of the carrier part having the above-described structure, Wang Resin is preferably exemplified. For example, it is 4-(hydroxymethyl)phenoxymethylpolystyrene resin.

Further, from the viewpoint of more reliably obtaining catalysts for a cross-coupling reaction having a structure of the formula (P2), the formula (P3), and the formula (P4), it is preferable that the organometallic complex serving as a precursor of the organometallic complex part represented by the formula (M1) has a structure of the following formula (M9).

[Chemical 23]

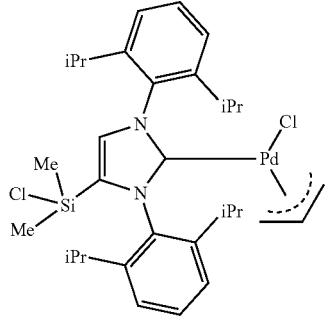

(M9)

In the formula (M9), Pr represents an isopropyl group, and Me represents a methyl group.

<Preferred Embodiments of the Method for Producing a Catalyst for a Cross-Coupling Reaction>

The method for producing the catalyst for a cross-coupling reaction of this embodiment is not particularly limited and the catalyst can be produced by combining and optimizing a known method for synthesizing a ligand and a method for synthesizing a complex catalyst.

As described above, the catalyst for a cross-coupling reaction of this embodiment can be produced by performing a condensation reaction represented by the previously described formula (M3) using the organometallic complex of the precursor of the organometallic complex part (having the structure represented by the formula (M1)) and the synthetic resin precursor of the precursor of the carrier part (having the structure represented by the formula (M2)) as reactants.

The organometallic complex of the precursor of the organometallic complex part having the structure represented by the formula (M1) can be produced with reference to, for example, the methods described in Patent Document 1 and Patent Document 2.

For example, the organometallic complex of the precursor of the organometallic complex part having a structure represented by the formula (M9), which has a preferred form, can be produced through three steps shown in the following formula (R01), the formula (R02) and the formula (R03).

[Chemical 24]

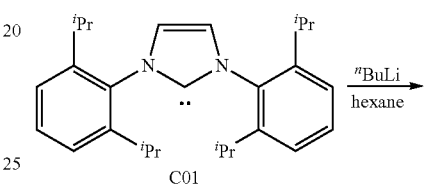

(R01)

[Chemical 25]

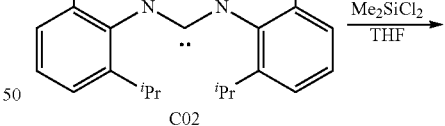

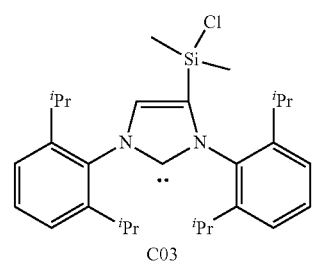

[Chemical 26]

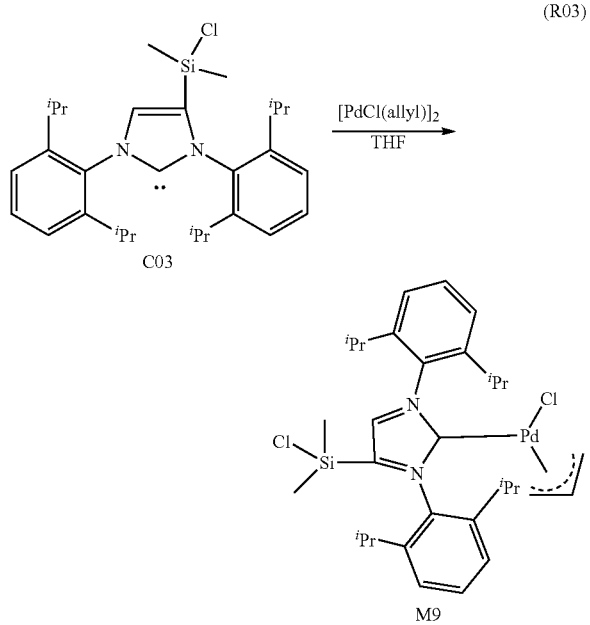

(R03)

Here, in the formula (R02), THF represents tetrahydrofuran.

Also, the compound C01 in the formula (R01) can be obtained commercially. For example, there can be exemplified 1, 3-Bis (2, 6-diisopropylphenyl)imidazol-2-ylidene (CAS RN: 244187-81-3, Product code: B3465) available from TCI.

Further, from the organometallic complex of the precursor of the organometallic complex part having the structure represented by the formula (M9) and Wang Resin (a suitable example of the synthetic resin precursor of the precursor of the precursor of the carrier part), a preferred embodiment of a catalyst for a cross-coupling reaction of the present invention having a structure represented by the formula (P4) (e.g., a product name: "DMSO-PDA" available from N.E. CHEMCAT CORPORATION) can be synthesized through a reaction step represented by the following formula (R04).

[Chemical 27]

(R04)

P4

EXAMPLE

The present invention is further illustrated by the following examples, which are not intended to be limiting.

Figure 9:
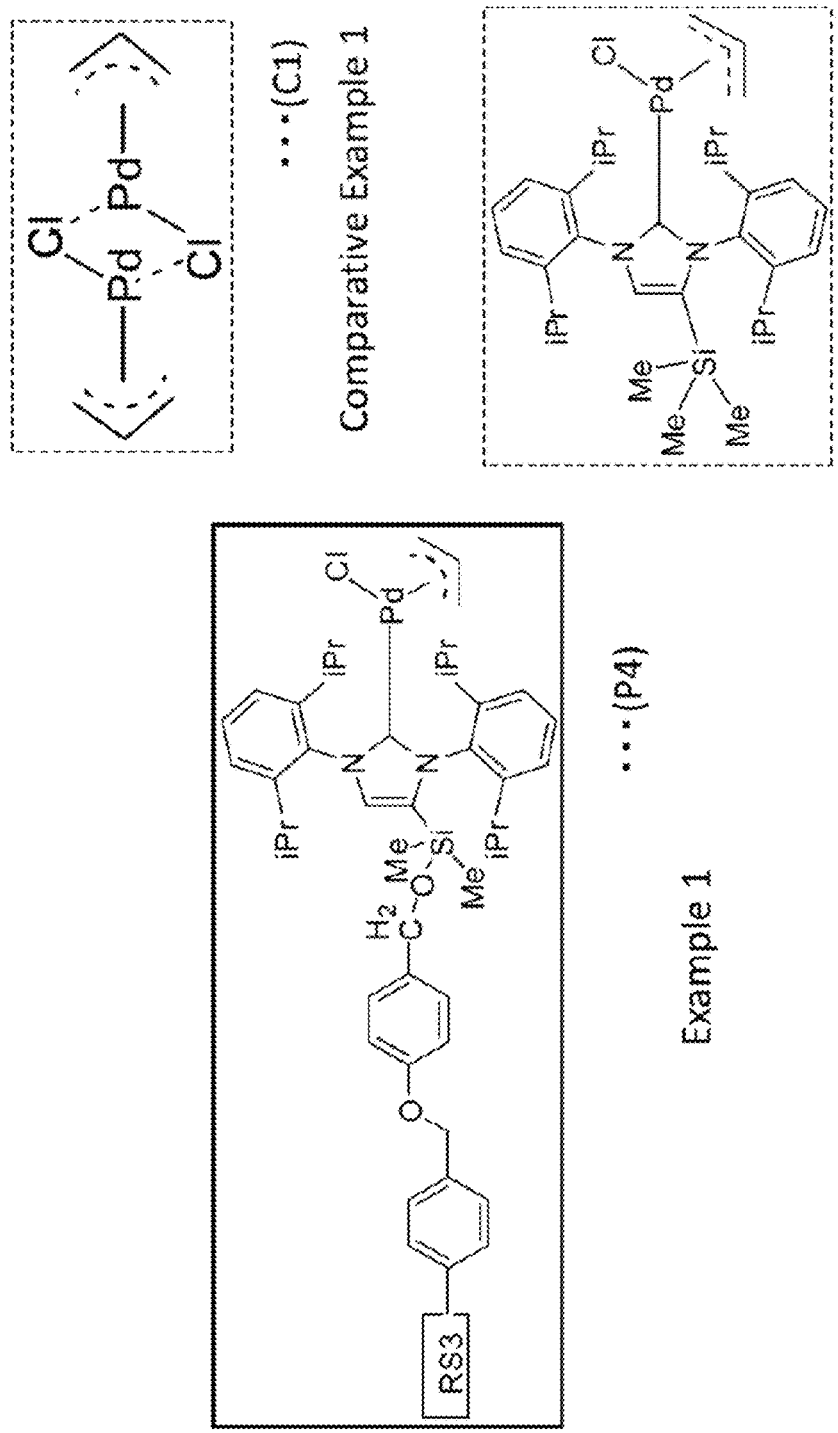
FIG. 9 is an explanatory view representing the chemical formulae of the catalysts for a cross-coupling reaction of Example 1, Comparative Example 1, and Reference Example 1.

Specifically, catalysts for a cross-coupling reaction of Example 1, Comparative Example 1, and Reference Example 1 represented by the chemical formulae (P4), (C1) and (C2) shown in FIG. 9 were prepared.

(Description of Analyzer)

As for the analysis in synthesizing the catalysts for a cross-coupling reaction of Example 1, Comparative Example 1, and Reference Example 1 described below, the following apparatus was used.

[Nmr Spectrum]

Bruker Biospin Avance400 (400 MHz) manufactured by Bruker Corporation was used to measure $^1$H NMR, $^{13}$C{$^1$H}NMR and $^{29}$Sis{$^1$H}NMR spectrum. For all measurements of the ligands, a dehydrated heavy solvent was used. This was for the prevention of ligand decomposition.

For measuring $^{13}$C{H}CPMAS and $^{29}$Si{$^1$H}CPMAS spectrum, Bruker Avance400WB (400 MHz) manufactured by Bruker Corporation was used.

[Mass Spectrometry]

MALDI-TOF-MS spectrum was measured by using AUTOFLEX™TOF/TOF manufactured by Bruker Corporation was used.

[Elemental Analysis]

Elemental analyses were conducted by using FLASH EA 1112SERIES elemental analyzer manufactured by Thermo Fisher Scientific K.K.

[Gc Measurement]

Gas chromatography (GC) measurement was conducted by using a GC-2014 manufactured by SHIMADZU CORPORATION. For the capillary column, TC-1 (60 m) was used.

(Description of Commercially Available Reagents)

In the synthesis and analysis of the catalysts for a cross-coupling reaction of Example 1, Comparative Example 1, and Reference Example 1 described below, the following commercially available reagents were used.

Reagents manufactured by Tokyo Chemical Industry Co., Ltd.: 4-(hydroxymethyl)phenoxymethylpolystyrene resin, 1,3-di-tertbutylimidazole-2-ylidene, chlorobenzene, 4-chloroanisole, 2-chloropyridine, 4-chlorotoluene, morpholine, dibutylamine, N-methylaniline, aniline diphenylamine, potassium tert-butoxide, sodium tert-butoxide, dodecane Reagent manufactured by KANTO CHEMICAL CO., INC.: n-butyllithium Reagents manufactured by Sigma-Aldrich Japan: dichlorodimethylsilane, heavy benzene, heavy tetrahydrophthane Reagents manufactured by Wako Pure Chemical Industries, Ltd.: allylpalladium (II) chloride dimer, tetrahydrofuran, hexane, toluene

Reference Example 1

An organometallic complex catalyst (trade name "NTMS-PDA", manufactured by N.E. CHEMCAT CORPORATION (hereinafter referred to as "$^{TMS}$IPrPd(allyl), if necessary, represented by the product C2 in the following formula (R07)) was prepared by the following procedure.

Here, "TMS" represents a trimethylsilyl group. In addition, "IPr" represents a ligand (1,3-bis(2,6-diisopropylphenyl)imidazole-2-ylidene) having an NHC structure represented by the following formula (C01). First, the method described in the scientific literature (Wang, Y., Xie, Yaming., Abraham, M. Y., Wei, P., Schaeferlll, H. F., Schleyer, P. R., Robinson, G. H. J. Am. Chem. Soc. 2010, 132, 14370) was improved and, through two steps represented by the following reaction formula (R05), a ligand C04 was synthesized in which a trimethylsilyl group (—SiMe$_3$, "TMS group") was bonded to a carbon at the 4-position in an NHC structure of an IPr (ligand represented by the formula (C01)). Aa the IPr, a commercially available product (1, 3-Bis (2, 6-diisopropylphenyl)imidazol-2-ylidene(CAS RN: 244187-81-3, product code: B3465) manufactured by TCI) was used.

[Chemical 28]

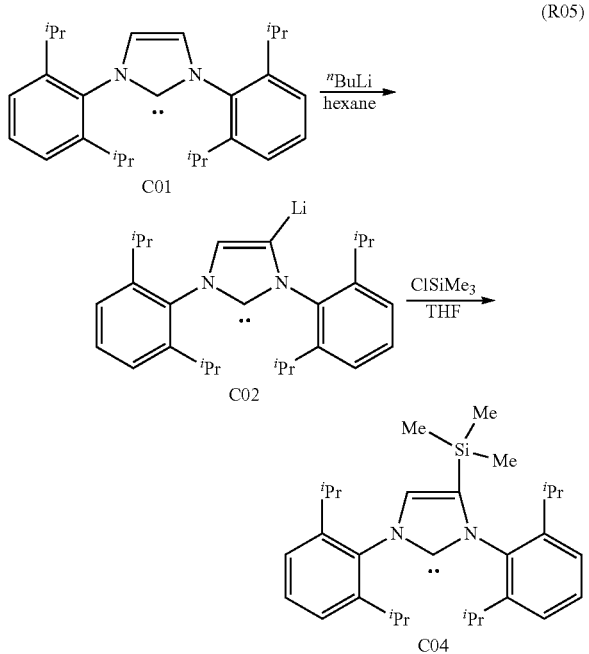

In formula (R05), $^n$BuLi represents CH$_3$CH$_2$CH$_2$CH$_2$Li and THF represents tetrahydrofuran.

An example of the procedure for synthesizing the intermediate product C02 (Li-IPr) in the formula (R05) will be explained. First, 10.79 g (27.62 mmol) of IPr (reactant 3) and 100 mL of dehydrated hexane were added into a 300 mL eggplant flask in a glove box, and the obtained solution was stirred at room temperature for 30 minutes. Next, nBuLi was slowly added dropwise to the obtained suspension and the suspension was stirred continuously overnight at room temperature to react. In this reaction, a slurry-like solution having pale brown color was changed to a slurry-like solution having yellow color. After completion of the reaction, the solution was filtrated through a membrane filter and washing was conducted with dehydrated hexane. The resulting yellow powder solid content {intermediate product 4 (Lithio compound: Li-IPr) in the formula (R$^4$)} was dried.

The yield amount of the intermediate product C02 (yellow powder solid content) in the formula (R05) was 10.0 g and its yield was 92.0%.

Next, a procedure for synthesizing the product (C04) in the formula (R05) will be explained.

First, 0.78 g (1.98 mmol) of the intermediate product C02 (Li-IPr) and 25 mL of dehydrated THF were added and dissolved in 50 mL Schlenk in a glove box. Next, 0.26 ml (2.04 mmol) of chlorotrimethylsilane (CiSiMe$_3$, hereinafter referred to as "ClTMS" if necessary) was slowly added dropwise, the reaction was allowed to proceed for 25 minutes, and after completion of the reaction, the solvent was removed.

In a glove box, 10 mL of dehydrated toluene was added to the solid product to dissolve, and the obtained liquid was transferred to a centrifuge tube. A centrifugation treatment was conducted on the liquid in the centrifuge tube at 4000 rpm for 6 minutes at room temperature to separate a salt (LiCl). Next, the obtained filtrate was passed through a filter (manufactured by Advantec Co., Ltd., 0.2 μm) and separated into 50 mL Schlenk. The, the removal of solvent was conducted to obtain a yellow powdery solid content ($^{TMS}$IPr, i.e., object ligand C04).

The yield amount of the product C04 "$^{TMS}$IPr" (yellow powdery solid content) in the formula (R05) was 0.901 g and its yield was 98.9%.

Identification was conducted by using $^1$H NMR, and it was confirmed that the lithiation of hydrogen atom bonded to carbon at the 4-position in the NHC-structure of IPr (reactant C01) progressed, and $^{TMS}$IPr (object ligand C04) was synthesized.

Next, with reference to Non-Patent Document 9, a n allyl Pd complex {(allyl) palladium (II) chloride, hereinafter, [(allyl)PdCl]$_2$, if necessary," }, which is a Pd source, was synthesized by a reaction represented by the following formula (R06).

[Chemical 29]

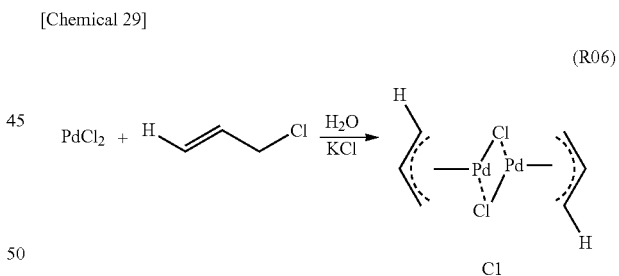

The procedure for synthesizing the product C1 in the formula (R06), i.e., the n allyl Pd complex {[(allyl)PdCl]$_2$} will be explained.

To 500 mL Schlenk was added distilled water (260 mL) and bubbling with Ar was conducted for 30 min. Then, PdCl (2.14 g, 12.0 mmol) and KCl (1.89 g, 24.0 mmol) were added and stirring was conducted at room temperature for 1 hour. The liquid changed from a slurry state to a brown transparent liquid before and after stirring. To this liquid, allyl chloride (2.96 mL, 36.0 mmol) was added dropwise, and the liquid was further stirred at room temperature overnight to proceed the reaction of the formula (R06). After completion of the reaction, the reaction mixture was extracted 5 times with 30 ml of chloroform, and the extracted chloroform was dried with MgSO$_4$. Next, filtration and solvent removal were conducted on the obtained liquid to obtain a yellow solid content (π allyl Pd complex C1).

The yield amount of π-allyl Pd complex C1 was 2.09 g and its yield was 94.9%.

Identification was conducted by using a 1H NMR and it was determined that the π-allyl Pd complex C1, which was an object compound, could be synthesized because the chemical shifting and integral value were coincided with the that described in Non-Patent Document 9.

The measurement result of the n allyl Pd complex C1 is shown below.

$^1$H NMR (CDCl$_3$, 400 MHz): δ=5.45 (m, 2H), 4.10 (d, 4H, J=6.7 Hz), 3.03 (d, 4H, J=12.1 Hz)

Next, a reaction represented by the following reaction formula (R07) was conducted by using a ligand C04 ($^{TMS}$IPr) having an NHC-structure and a π-allyl Pd complex C1 to synthesize a product C2 serving as an organometallic complex catalyst of Reference Example 1, i.e., "$^{TMS}$"IPrPd (allyl).

This process was based on reaction conditions originally examined by the present inventors.

[Chemical 30]

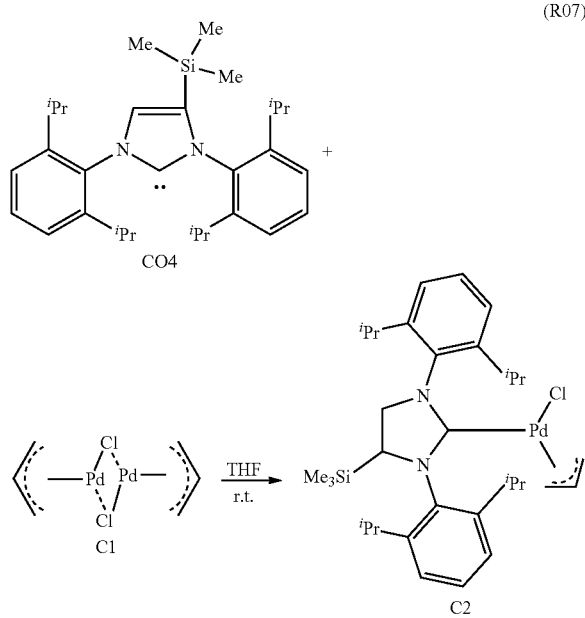

In a glove box, 0.90 g (1.95 mmol) of the ligand C04 ($^{TMS}$IIPr) having an NHC-structure and 15 mL of dehydrated THF were added to 50 ml Schlenk. Then, 10.36 g (0.98 mmol) of π-allyl Pd complex C and 10 mL of dehydrated THF were added to 20 mL vials. A solution of the π-allyl Pd complex C1 was added dropwise to a solution of TMS IPr {reactant C04 in the formula (R07)}. The resulting liquid was stirred at room temperature for 1 hour. The color of the liquid changed from orange to brown before and after stirring. Next, the liquid was passed through a powder of activated carbon to remove Pd black generated by the reaction. At this time, the color of the liquid changed to yellow after passing through the activated carbon. THF was then completely removed from the resulting liquid. Then, a small amount of dehydrated hexane was added and powdered. The resulting solid content was washed with hexane to obtain a yellow solid content {product C2 in the formula (R07), i.e., $^{TMS}$IPrPd(allyl)}.

Next, purification was conducted by a recrystallization treatment using hexane or the like for the organometallic complex catalyst C2 (yellow solid content) serving as Reference Example 1.

Note that this organometallic complex catalyst C2 was synthesized for the first time by the present inventors as an organometallic complex catalyst used in a cross-coupling reaction.

The yield amount of the organometallic complex catalyst C2 (yellow powdery solid content) was 0.84 g and its yield was 66.8%

The identification of the organometallic complex catalyst C2 was confirmed by $^1$H NMR, $^{13}$C{1H}NMR, $^{29}$Si{$^1$H}NMR, MALDI-TOF-MS and the elemental analyses.

The measurement result of the organometallic complex catalyst C2 are shown below. The spectrum of MALDI-TOF-MS is shown. Table 1 represents the result of the elemental analysis.

1H NMR (CDCl$_3$, 400 MHz): δ7.37-7.44 (m, 2H), 7.23-7.28 (m, 4H), 7.18 (s, 1H), 4.80 (m, 1H), 3.93 (d, 1H, J=7.2 Hz), 3.12 (m, 2H), 2.97 (m, 2H), 2.82 (d, 1H, J=13.5 Hz), 2.75 (m, 1H), 1.59 (d, 1H, J=11.8 Hz), 1.36 (m, 12H), 1.19 (m, 12H), 0.09 (s, 9H)

$^{13}$C{$^1$H} NMR (CDCl$_3$, 100 MHz): δ188.2, 146.5, 146.2, 145.9, 145.6, 137.6, 136.1, 135.8, 133.4, 130.0, 129.8, 129.7, 124.2, 124.1, 123.7, 114.2, 73.2, 50.0, 28.8, 28.4, 28.2, 26.5, 25.7, 25.6, 25.3, 24.7, 26.1, 23.3, 0.1

$^{29}$Si{$^1$H} NMR (CDCl$_3$, 80 MHz):δ-8.1

TABLE 1

| C$_{33}$H$_{49}$ClN$_2$PdSi | C[%] | H[%] | N[%] |
| --- | --- | --- | --- |
| Calculated value | 61.57 | 7.67 | 4.35 |
| Measured value | 61.56 | 7.64 | 4.14 |

From $^1$H NMR result, a peak derived from the allylic group was observed in the organometallic complex catalysts C2, and the integrated value coincided with the object structure. A clean one signal was also observed from the $^{29}$Si{$^1$H}NMR. Further, the detailed assignment of 1H NMR and $^{13}$C{$^1$H}NMR were determined from $^1$H-$^1$H correlation, $^1$H-$^{13}$C correlation, and 13C DEPT spectrum.

As shown in Table 1, it was judged that the organometallic complex catalyst C2 as the object compound could be synthesized because the calculated value and the actual measurement value relating to the elemental analysis were almost consistent (difference within 0.3%).

Further, from the result of MALDI-TOF-MS, it was observed that Cl was removed from Pd by the laser. The result of MALDI-TOF-MS indicated that the ligand having an NHC-structure and Pd were bonded, and it was judged that the object organometallic complex catalyst C2 could be synthesized from this viewpoint as well.

Example 1

A catalyst for a cross-coupling reaction represented by the formula (P4) (product name: "DMSO-PDA" manufactured by N.E. CHEMCAT CORPORATION) was prepared.

The organometallic complex represented by the formula (M9) was synthesized through the steps of the formula (R01) to the formula (R03) described as above on the basis of the production method described in Reference Example 1. For the compound C01 in the formula (R01), commercially available 1, 3-Bis (2, 6-diisopropylphenyl)imidazol-2- ylidene(CAS RN: 244187-81-3, product code: B3465) manufactured by TCI was used.

The organometallic complex represented by the formula (M9) was identified by measuring 1H NMR spectrum, measuring the $^{13}C\{^1H\}$ NMR spectrum, and measuring the $^{29}Si\{^1H\}$ NMR spectrum.

Figure 2:
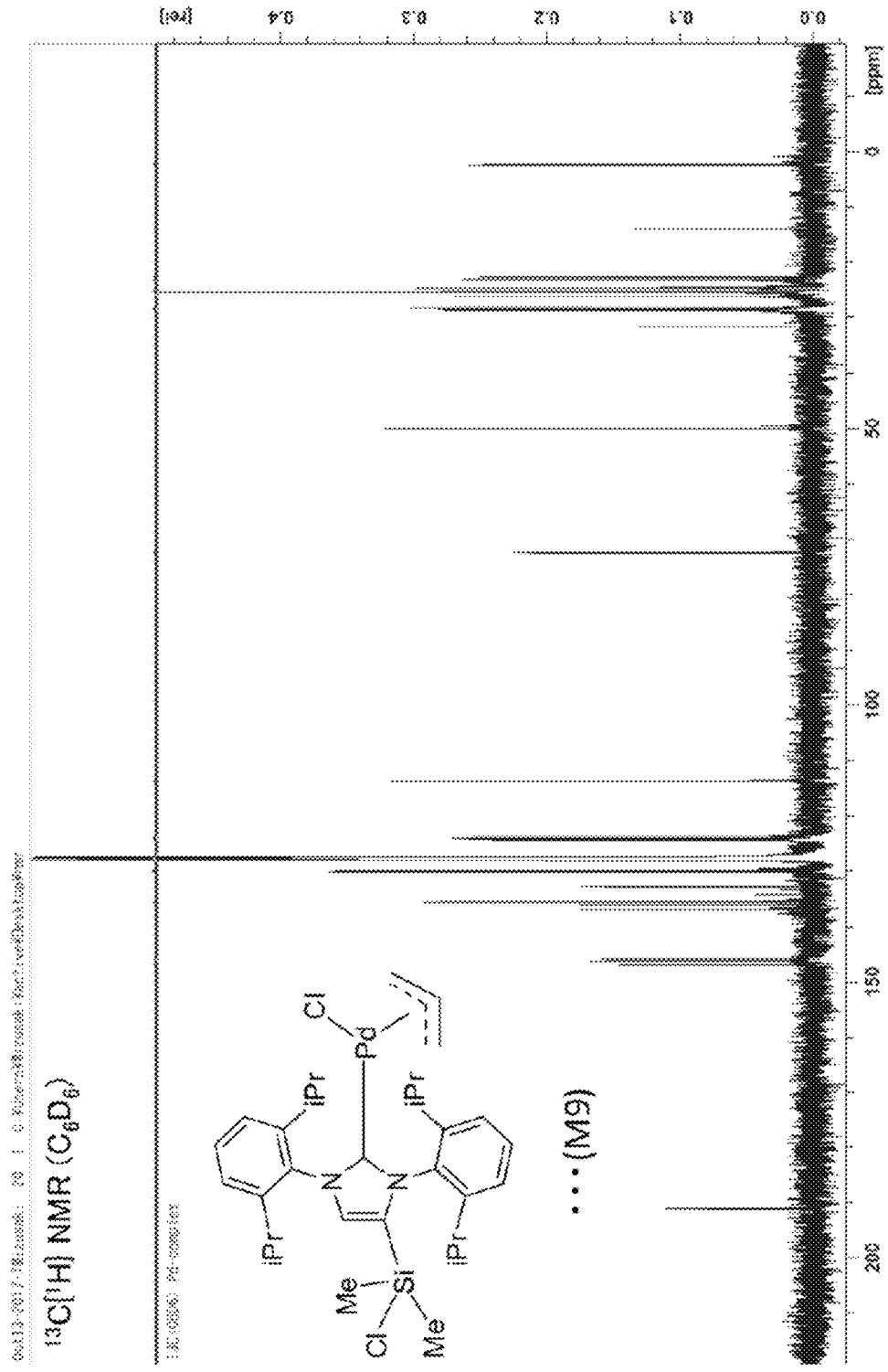
FIG. 2 is a graph representing a $^{13}$C{$^1$H}NMR spectrum obtained for the organometallic complex (an organometallic complex represented by the formula (M9)) serving as a precursor (raw material) of the organometallic complex part of the cross-coupling reaction catalyst of Example 1.

FIG. 1 represents a 1H NMR spectrum obtained for the organometallic complex represented by the formula (M9). FIG. 2 represents a $^{13}C\{^1H\}$ NMR spectrum obtained for the organometallic complex represented by the formula (M9). Further, FIG. 3 represents the $29Si\{1H\}$ NMR spectrum obtained for the organometallic complex represented by the formula (M9).

Figure 3:
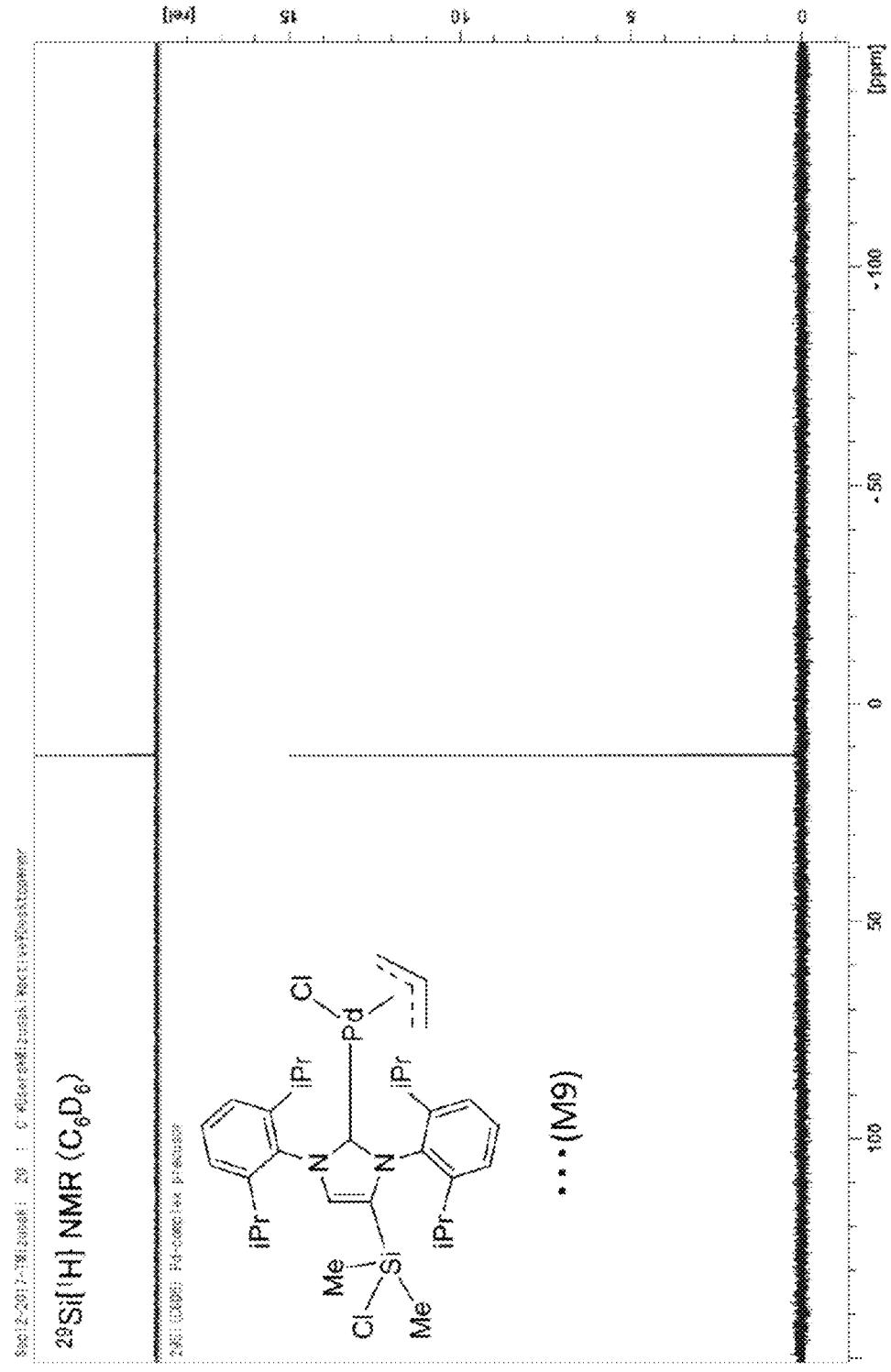
FIG. 3 is a graph representing a $^{29}$Si{$^1$H}NMR spectrum obtained for the organometallic complex (an organometallic complex represented by the formula (M9)) serving as a precursor (raw material) of the organometallic complex part of the catalyst for a cross-coupling reaction of Example 1.

The results of measuring $^1H$ NMR spectrum shown in FIG. 1, the result of measuring the $^{13}C\{^1H\}$ NMR spectrum shown in FIG. 2, and the result of measuring the $^{29}Si\{^1H\}$ NMR spectrum shown in FIG. 3 are shown in FIG. 4.

From the measurement results of these NMR spectra, it was confirmed that the organometallic complex shown by the formula (M9) could be synthesized.

Next, a catalyst for a cross-coupling reaction represented by the formula (P4) was synthesized by the synthesis shown by the formula (R04) using an organometallic complex represented by the formula (M9) and commercially available Wang Resin.

$^{13}C$ CPMAS spectrum, $^{29}Si$ CPMAS spectrum, $^{29}Si$ spectrum were measured to identify the catalyst for a cross-coupling reaction of Example 1 represented by the formula (P4).

FIG. 5 shows $^{13}C$ CPMAS spectrum obtained from Wang resin (FIG. 5A), and $^{13}C$ CPMAS spectrum obtained from the catalyst for a cross-coupling reaction of Example 1.

FIG. 6 represents $^{29}Si$ CPMAS spectra obtained for the catalysts for cross-coupling reactions of Example 1.

FIG. 7B and FIG. 7B show $^{29}Si\{^1H\}$ NMR spectrum (FIG. 7A) obtained from the precursor of the organometallic complex part and $^{29}Si$ CPMAS spectrum (FIG. 7B) obtained from the catalyst for a cross-coupling reaction of Example 1.

FIG. 8 is a graph showing the measurement result of X-ray photoelectron spectroscopy (XPS) obtained from the catalyst for a cross-coupling reaction of Example 1.

From the comparison of FIG. 5A and FIG. 5B, in the $^{13}C$ CPMAS spectrum of the catalyst for a cross-coupling reaction of Example 1, peaks attributed to alkyl group (iPr group) which was not observed in the $^{13}C$ CPMS spectrum of Wang resin was observed at around 30 ppm.

Aa shown in FIG. 6, from $^{29}Si$ CPMAS spectrum of the catalyst for a cross-coupling reaction of Example 1, a peak assigned to Si of silanol group was observed at around 0 ppm.

From the comparison of FIG. 7A and FIG. 7B, the peak assigned to Si of silanol group observed in $^{29}Si\{^1H\}$ NMR spectrum of the precursor of the organometallic complex part of the formula (M9) is shifted in the negative direction (the direction in which the electron density of Si increases) in $^{29}Si$ CPMAS spectrum of the catalyst for a cross-coupling reaction of Example 1.

In the mixture of Wang resin and the precursor of the organic metal complex part of the formula (M9), this peak attributed to Si does not shift. Further, it is inferred, from the fact that the peak attributed to Si is shifted in the direction of increasing the electron density of Si, that Si of silanol group of the precursor of the organometallic complex part of the formula (M9) is in the state in which it is bonded to the electron-withdrawing Cl but Cl is desorbed with the progress of the condensation reaction represented by the formula (R04) and the electron-donating end of Wang resin is bonded to the Si. That is, it is considered that the precursor of the organometallic complex part of the formula (M9) is immobilized on Wang resin (carrier part) by chemical bonding.

From the measurement result of XPS in FIG. 8, the presence of Pd (divalent) instead of Pd (zero valent) was observed in the organometallic complex part of the catalyst for a cross-coupling reaction of Example 1 represented by the formula (P4). That is, it is considered that Pd of the coordination center exists in a state similar to $PdCl_2$ and that the Pd does not fall off from the organometallic complex part and exists as the coordination center inside the organometallic complex part.

Comparative Example 1

An organometallic complex catalyst represented by C1 in the formula (R06) (trade name "allylpalladium chloride dimer" manufactured by Wako Pure Chemical Industries, Ltd.) was prepared.

<Evaluation of Catalytic Activity by Cross-Coupling Reaction (1)>

Figure 10:
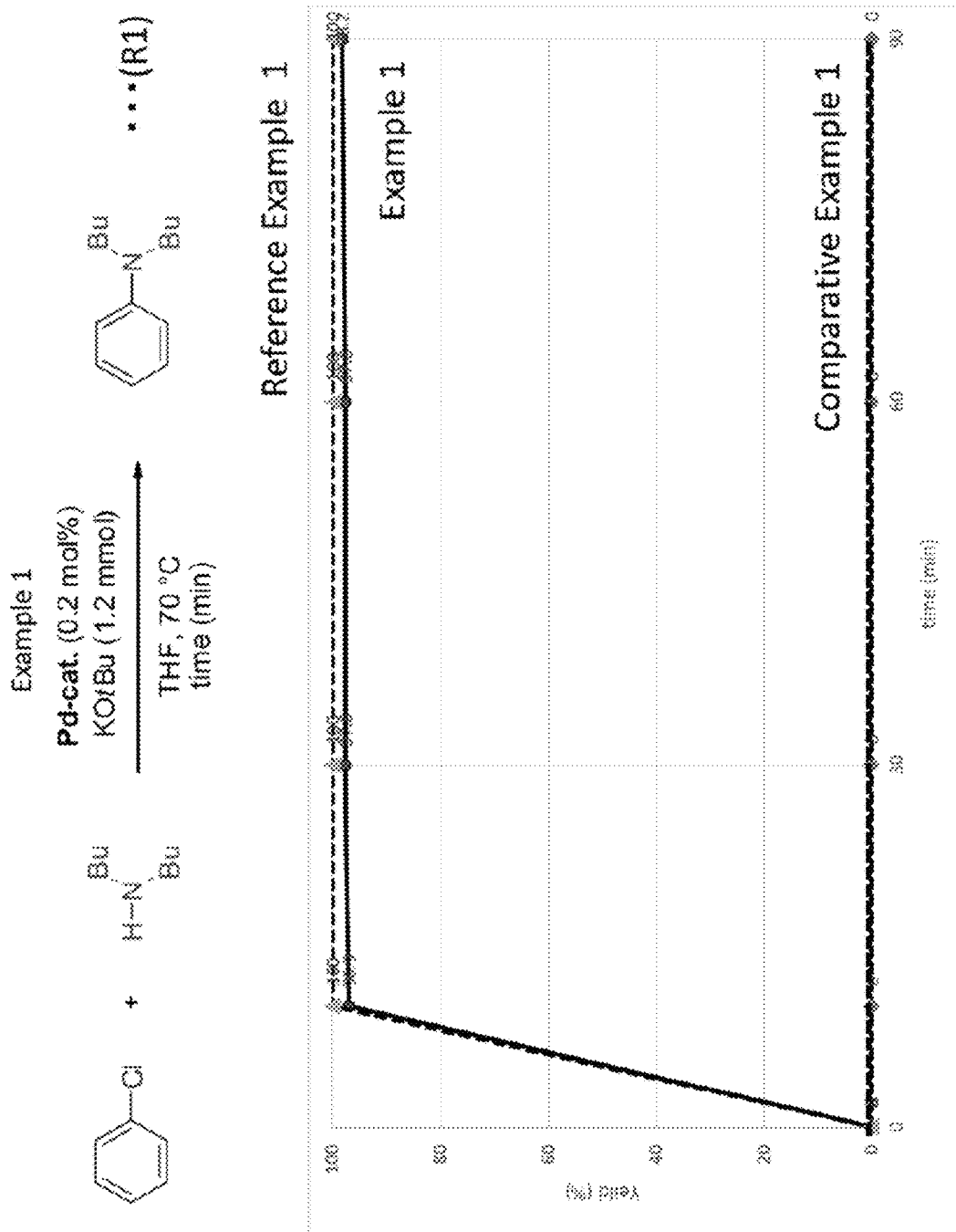
FIG. 10 is a graph representing the time dependence of the yield of each product when the catalyst for a cross-coupling reaction of Example 1, Comparative Example 1 or Reference Example 1 is used in the cross-coupling reaction represented by the formula ($R^1$).

The C—N cross-coupling reaction (Buchwald-Hartwig reaction) shown by reaction formula (R1) represented in FIG. 10 was conducted using the catalysts for a cross-coupling reaction of Example 1, Comparative Example and Reference Example 1. Note that the catalyst for a cross-coupling reaction of Example 1 was described as "Pd-cat." in FIG. 10 (the same in the other figures).

As shown in the reaction formula (R1), chlorobenzene, N,N-dibutylamine were used as a substrate, $^tBuOK$ was used as a base, and THF was used as a solvent. The preparation and the reaction were all carried out in an inert gas ($N_2$) atmosphere in a glove box. Dodecane was used as the internal standard substance and the yield was calculated by GC.

As the reaction conditions, 4.9 mmol of N,N-dibutylamine, a temperature of 70° C., and 0.20 mol % of a catalyst amount were used with 5 mmol of chlorobenzene. A graph representing the time dependence of the yield of each product when the catalyst for a cross-coupling reaction of Example 1, Comparative Example 1, and Reference Example 1 is used is shown in FIG. 10.

It was clarified from the results shown in FIG. 10 that, when the catalyst for a cross-coupling reaction of Example 1 satisfying the constitution of the present invention is used, an object product is obtained in a very high yield and in a relatively short reaction time than C—N cross-coupling reaction, as compared with the catalyst for a cross-coupling reaction of Comparative Example 21.

In addition, it has been clarified that the catalyst for a cross-coupling reaction of Example 1 satisfying the constitution of the present invention can obtain an object product in a yield as high as that of the organometallic complex catalyst of Reference Example 1 having a structure similar to that of the part of the organometallic complex part thereof.

<Evaluation of Catalytic Activity by Cross-Coupling Reaction (2)>

Figure 11:
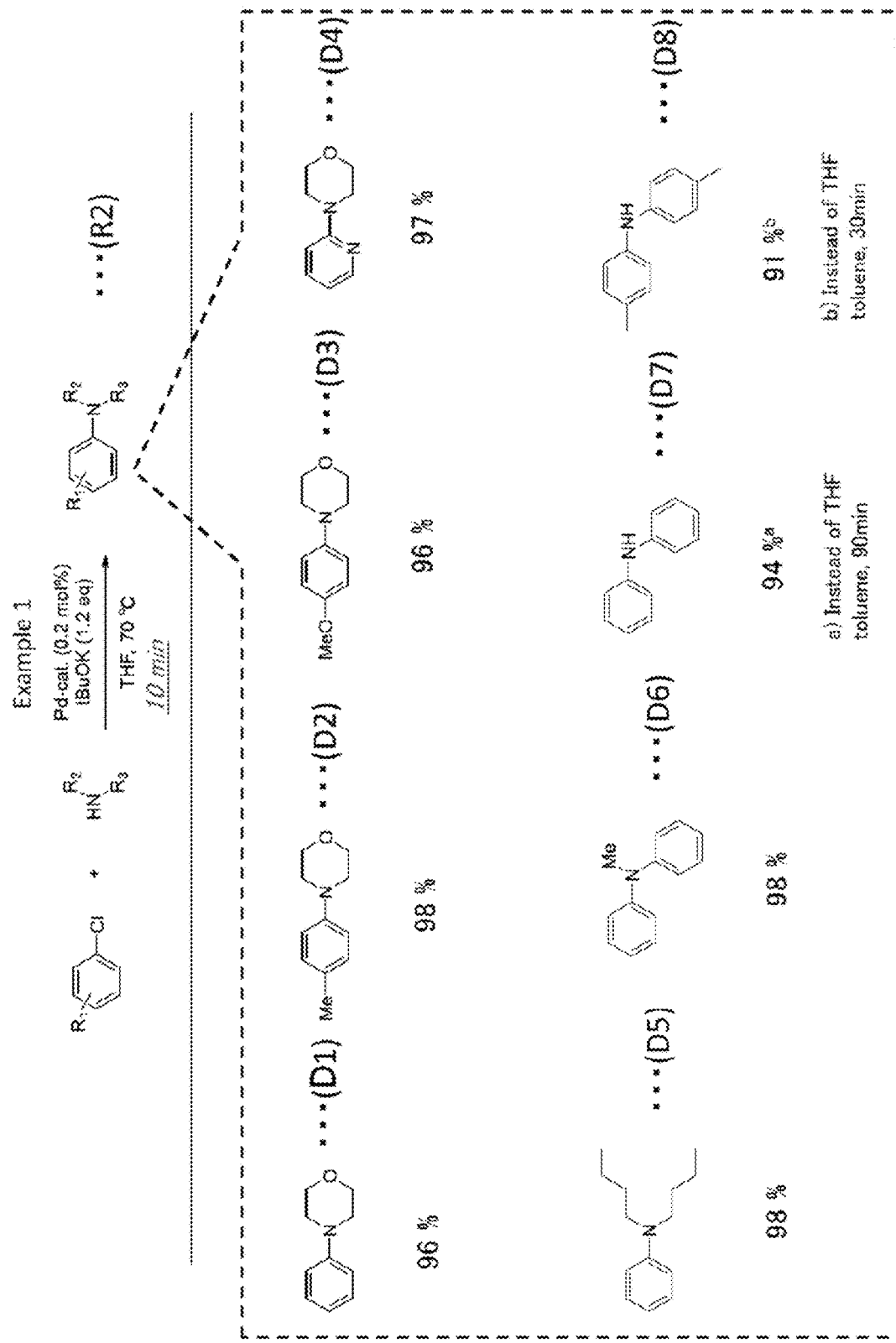
FIG. 11 is an explanatory view representing the yield of the product obtained when the catalyst for a cross-coupling reaction of Example 1 is used in the cross-coupling reaction represented by the formula ($R^2$).

Using the catalyst for a cross-coupling reaction of Example 1, the C—N cross-coupling reaction represented by the reaction formula (R2) shown in FIG. 11 was conducted.

As shown in the reaction formula (R2), various arylchlorides and morpholine were used as substrate, tBuOK was used as base, and THF was used as solvent. The preparation and the reaction were all conducted in an inert gas (N atmosphere in a glove box. Dodecane was used as the internal standard substance and the yield was calculated by GC.

As the reaction conditions, 4.9 mmol of morpholine, a temperature of 70° C. and 0.20 mol % of catalytic amount were used with 5 mmol of various arylchloride. The yields of the object products {compounds shown by formulas (D1) to (D8)} obtained for each cross-coupling reaction are shown in FIG. 11.

From the results shown in FIG. 11, it has been clarified that an object product can be easily obtained in a high yield and in a relatively short reaction time with a relatively small amount of use for the catalyst for a cross coupling reaction of Example 1.

In particular, as compared with the cross-coupling reaction described in Non-Patent Document 11, the reaction of the object product (D7) was conducted at a lower temperature, at a smaller catalyst use amount, in a short reaction time, and as a more difficult arylchloride as a reactant, so that the object product could be obtained in a yield higher than that reported in Non-Patent Document 11.

In addition, as compared with the cross-coupling reaction described in Non-Patent Document 12, the reaction of (D3) of the object product was conducted at a lower temperature, at a smaller catalyst use amount, in a short reaction time, and as a more difficult aryl chloride as a reactant, so that the object product could be obtained in a yield higher than that reported in Non-Patent Document 12.

Further, the reaction of the object product (D2) is conducted a reaction similar to the cross-coupling reaction described in Non-Patent Document 12, it was possible to obtain the object product in a high yield and in a short reaction time with a small amount of catalyst used.

<Evaluation of Catalytic Activity by Cross-Coupling Reaction (3)>

Figure 12:
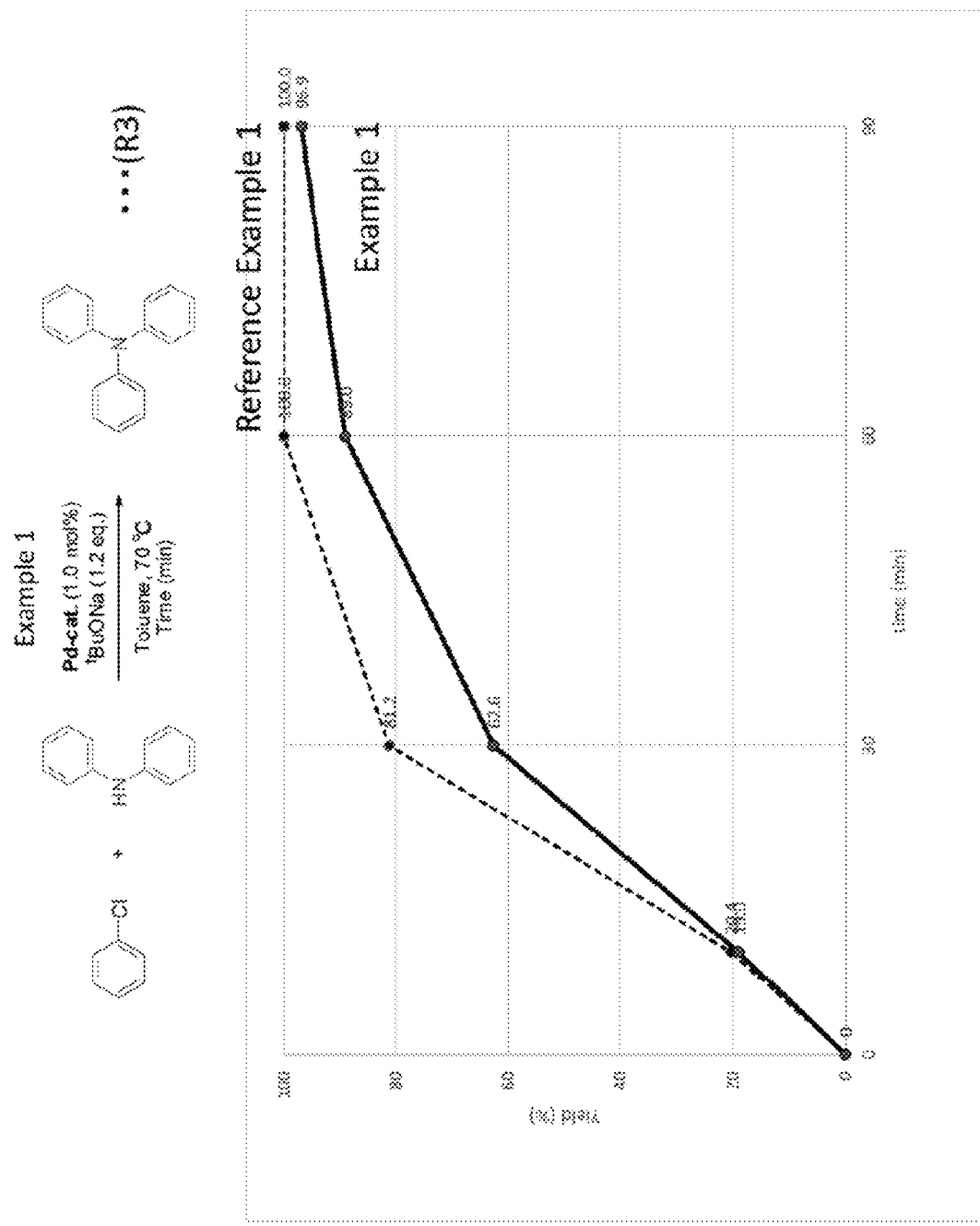
FIG. 12 is a graph representing the time dependence of the yield of each product when the catalyst for a cross-coupling reaction of Example 1 or Reference Example 1 is used in the cross-coupling reaction represented by the formula ($R^3$).

The C—N cross-coupling reaction represented by the reaction formula (R3) shown in FIG. 12 was conducted using the catalysts for a cross-coupling reaction of Example 1 and Reference Example 1.

From the result shown in FIG. 12, it has also been clarified that the catalyst for a cross-coupling reaction of Example 1 satisfying the constitution of the present invention can give the object product in a high yield and in a relatively short reaction time with a relatively small amount of use, even when compared with the organometallic complex catalyst of Reference Example 1, which has a structure similar to that of the part of the organometallic complex part thereof.

<Evaluation of Catalytic Activity by Cross-Coupling Reaction (4)>

Figure 13:
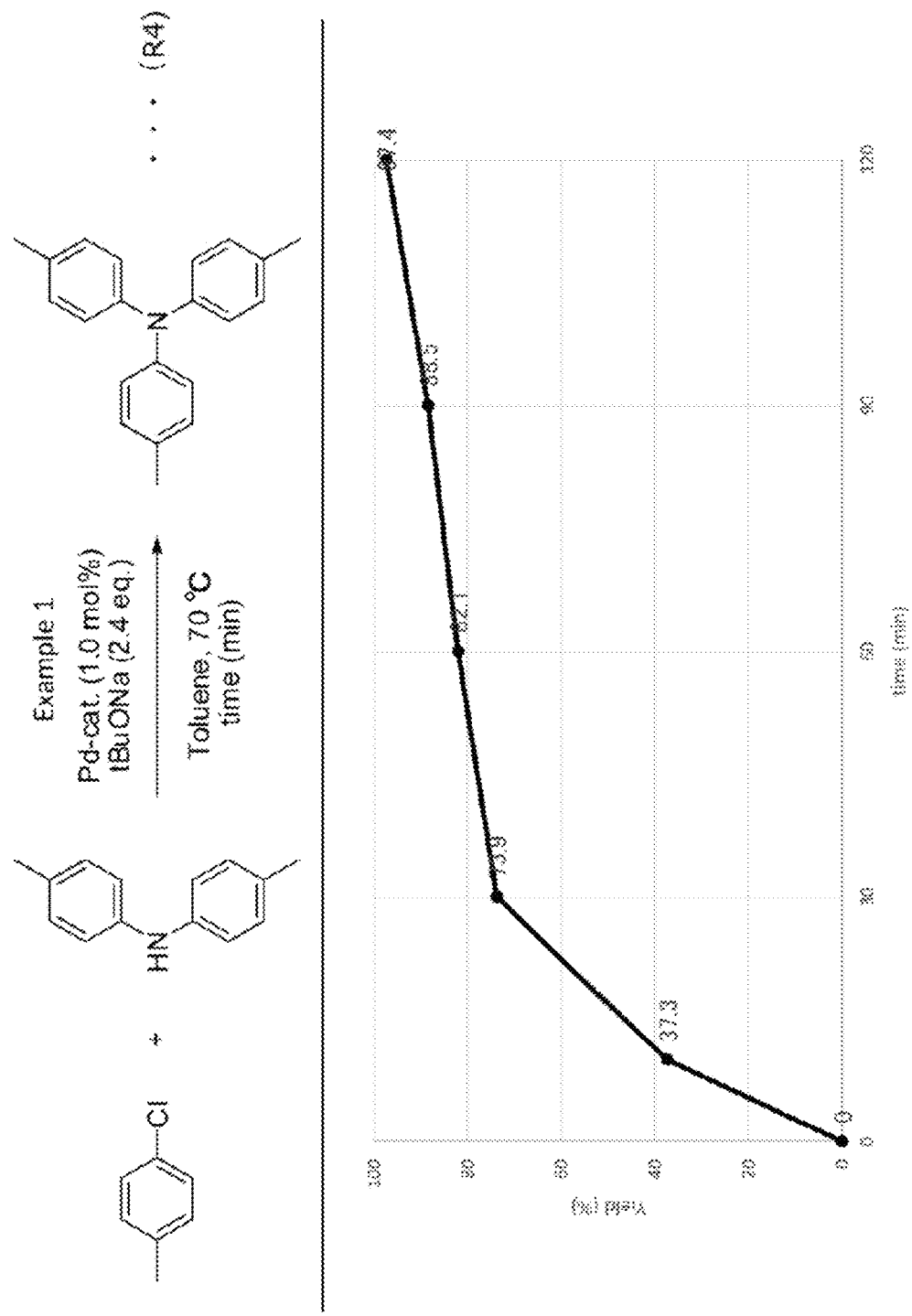
FIG. 13 is a graph representing the time dependence of the yield of the product when the catalyst for a cross-coupling reaction of Example 1 is used in the cross-coupling reaction represented by the formula ($R^4$).

Using the catalyst for a cross-coupling reaction of Example 1, the C—N cross-coupling reaction represented by the reaction formula ($R^4$) shown in FIG. 13 was conducted.

From the result shown in FIG. 13, it has also been clarified that the catalyst for a cross-coupling reaction of Example 1 satisfying the constitution of the present invention can give an object product in a high yield and in a relatively short reaction time with a relatively small amount of use.

<Evaluation of Catalytic Activity by Cross-Coupling Reaction (5)>

Figure 14:
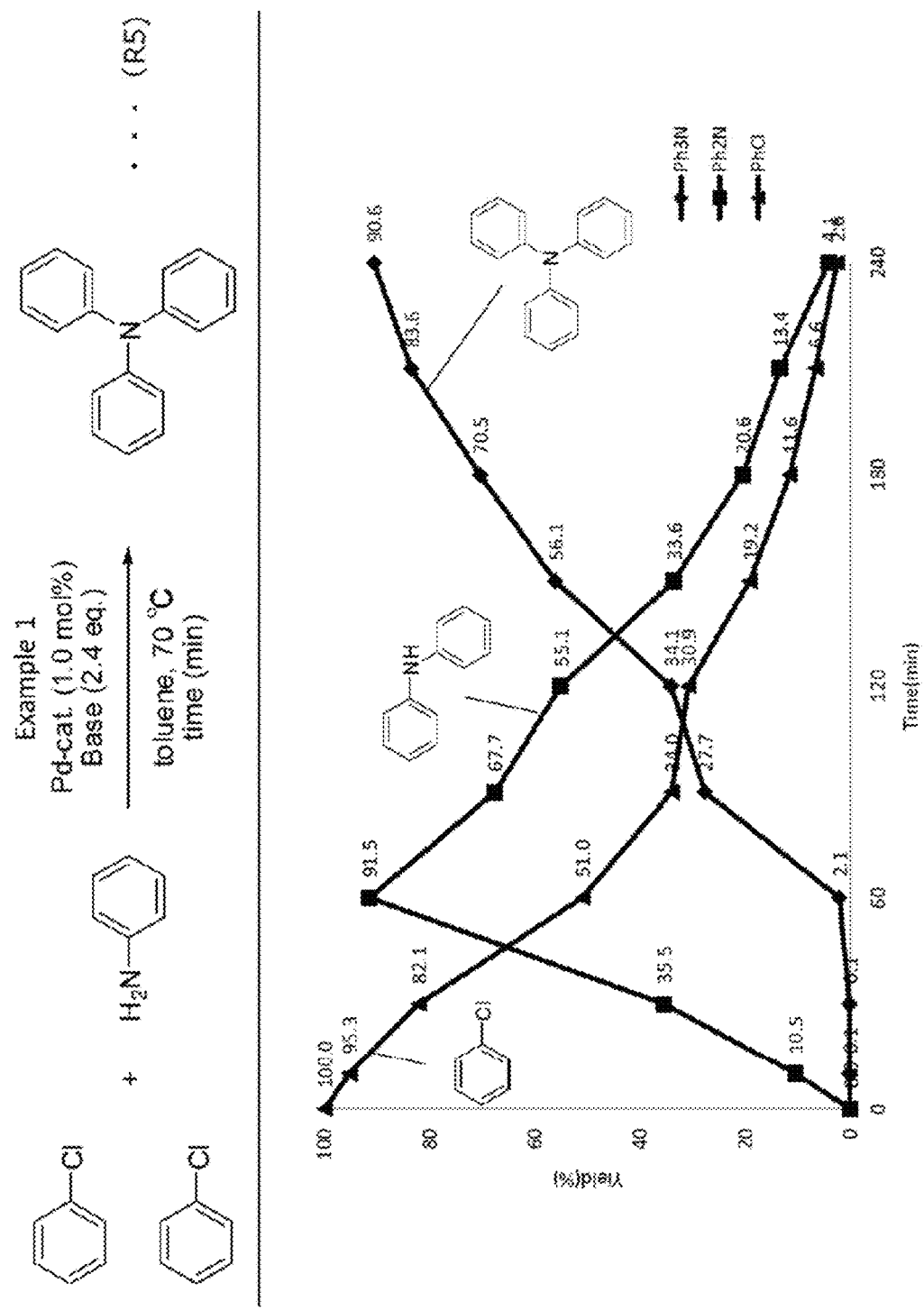
FIG. 14 is a diagram representing the time dependence of the yield of the product when the catalyst for a cross-coupling reaction of Example 1 is used in the cross-coupling reaction represented by the formula ($R^5$).

Using the catalyst for a cross-coupling reaction of Example 1, the C—N cross-coupling reaction represented by the reaction formula ($R^5$) shown in FIG. 14 was conducted.

From the result shown in FIG. 14, it has also been clarified that the catalyst for a cross-coupling reaction of Example 1 satisfying the constitution of the present invention can give an object product in a high yield and in a relatively short reaction time with a relatively small amount of use.

<Evaluation of Catalytic Activity by Cross-Coupling Reaction (6) and (7)>

Figure 15:
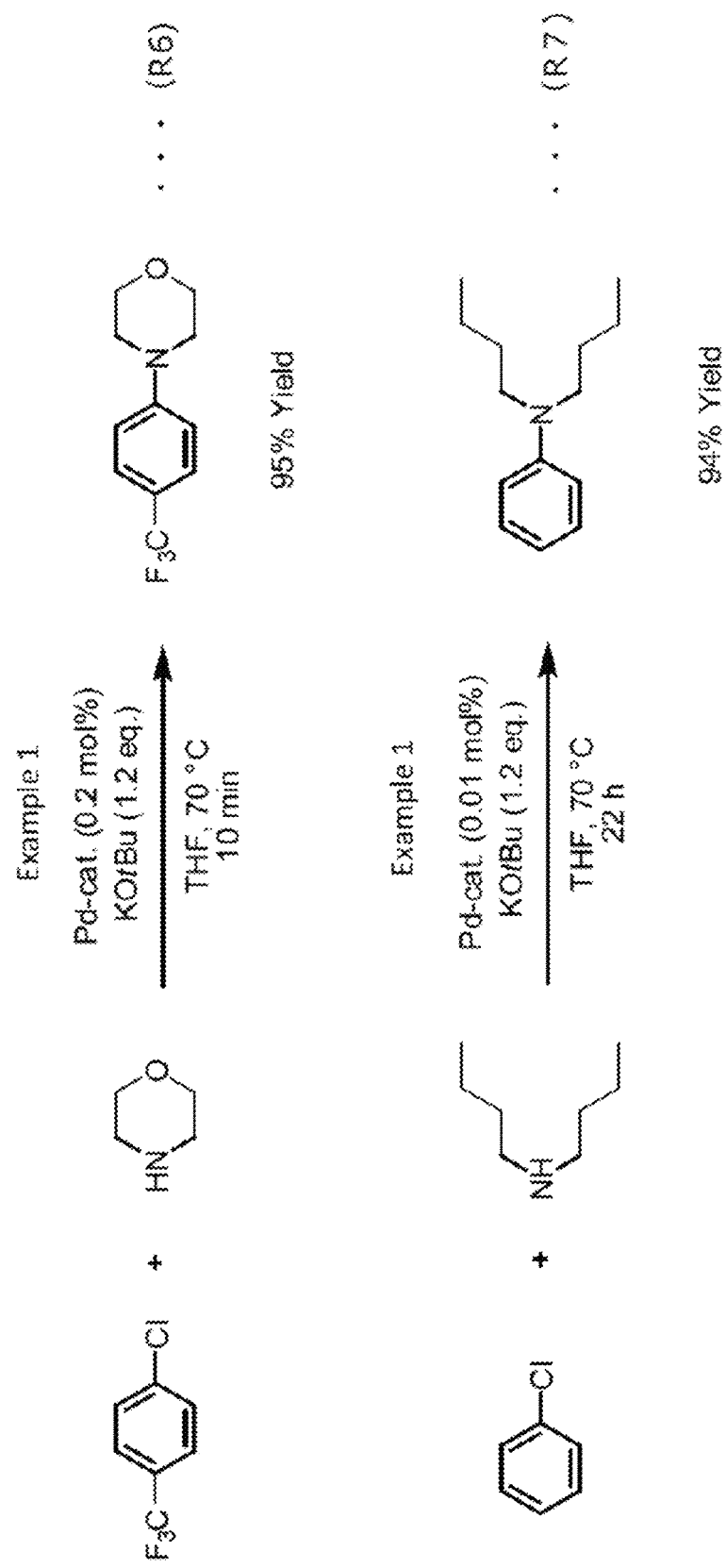
FIG. 15 is a diagram representing the yield of the product when the catalyst for a cross-coupling reaction of Example 1 is used in the cross-coupling reaction represented by the formulae ($R^6$) and ($R^7$).

The C—N cross-coupling reaction each represented by the reaction formulae (R6) or (R7) shown in FIG. 15 was conducted using the catalyst for a cross-coupling reaction of Example 1.

From the result shown in FIG. 15, it has also been clarified that the catalyst for a cross-coupling reaction of Example 1 satisfying the constitution of the present invention can give an object product in a high yield and in a relatively short reaction time with a relatively small amount of use.

INDUSTRIAL APPLICABILITY

In the catalyst of the present invention, an organometallic complex is sufficiently immobilized on a carrier, and an object product can be easily obtained in a high yield and in a relatively short reaction time with a relatively small amount of use. Thus, the present invention contributes to the development of mass production techniques in the field of pharmaceuticals, pesticides, and electronic materials in which cross-coupling is available for the synthesis of object products (e.g., aromatic amines).

The invention claimed is:
1. A catalyst for a cross-coupling reaction used in a cross-coupling reaction, the catalyst represented by formula (P1) which is obtained by a condensation reaction in accordance with an equation (M3),

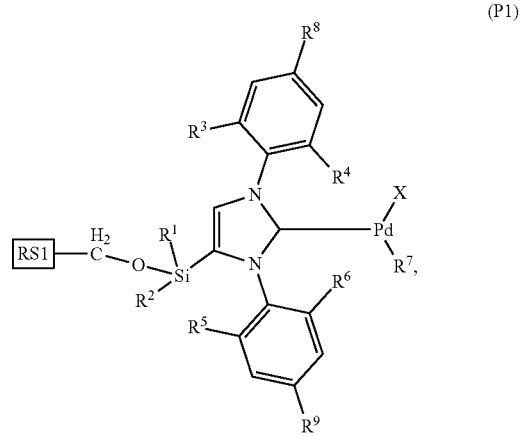

-continued

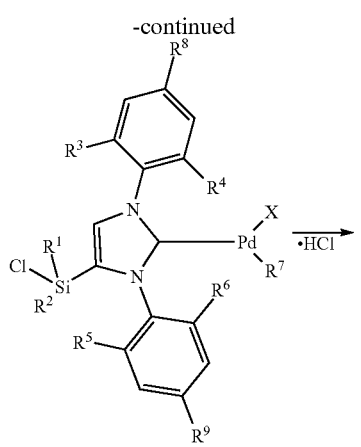

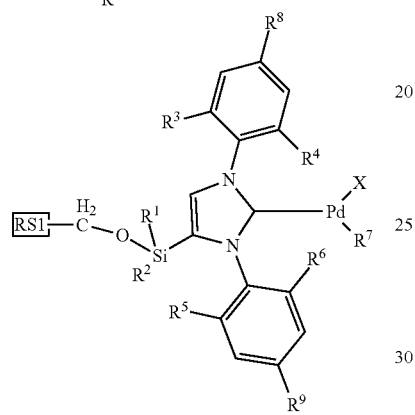

wherein, in the formula (P1) and the equation (M3),

R¹ and R² may be the same or different and are alkyl group,

R³, R⁴, R⁵, R⁶, R⁸ and R⁹ may be the same or different and are, respectively, at least one substituent selected from the group consisting of hydrogen atom, halogen atom, alkyl group, alkoxy group, alkenyl group, aryl group, hydroxy group, oxycarbonyl group, cyano group, formyl group, amino group, allyloxy group, nitro group, and silyl group, X represent a halogen atom, and R⁷ represents a substituent having carbon number of 3 to 20 with a π bond, or, a ligand selected from amine compound, phosphine compound, nitrile compound, or sulfur compound, the compound (M2) in the equation (M3) comprises a repeating unit represented by formula (M6) and a repeating unit represented by formula (M7):

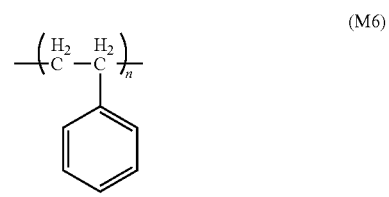

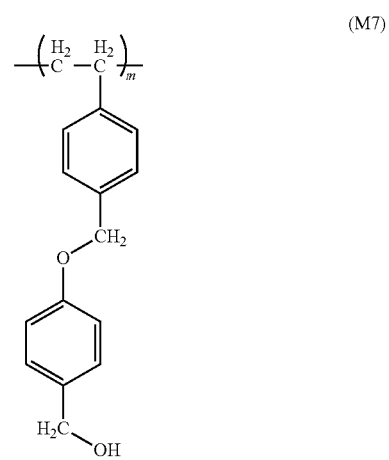

in which n is an integer of more than 1, and m is an integer of more than 1.

2. The catalyst for a cross-coupling reaction in accordance with claim 1, used for a C—N cross-coupling reaction.

3. The catalyst for a cross-coupling reaction used in a cross-coupling reaction, wherein the compound (M2) in the equation (M3) is a Wang Resin.

* * * * *